United States Patent
Prabhakarpandian et al.

(10) Patent No.: US 11,782,051 B2
(45) Date of Patent: Oct. 10, 2023

(54) SYSTEMS AND METHODS FOR REPERFUSION INJURY

(71) Applicant: CFD Research Corporation, Huntsville, AL (US)

(72) Inventors: Balabhaskar Prabhakarpandian, Madison, AL (US); Kapil Pant, Huntsville, AL (US); Kevin Daniel Roehm, Harvest, AL (US); Ketan Harendrakumar Bhatt, Huntsville, AL (US)

(73) Assignee: CFD RESEARCH CORPORATION, Huntsville, AL (US)

( * ) Notice: Subject to any disclaimer, the term of this patent is extended or adjusted under 35 U.S.C. 154(b) by 332 days.

(21) Appl. No.: 16/995,734

(22) Filed: Aug. 17, 2020

(65) Prior Publication Data
US 2020/0378952 A1 Dec. 3, 2020

Related U.S. Application Data

(60) Continuation-in-part of application No. 15/017,125, filed on Feb. 5, 2016, now Pat. No. 10,775,364, which
(Continued)

(51) Int. Cl.
G01N 33/50 (2006.01)
G01N 33/86 (2006.01)
B01L 3/00 (2006.01)

(52) U.S. Cl.
CPC ..... G01N 33/5029 (2013.01); G01N 33/5005 (2013.01); G01N 33/5011 (2013.01);
(Continued)

(58) Field of Classification Search
CPC ........... G01N 33/5029; G01N 33/5005; G01N 33/5011; G01N 33/5061; G01N 33/5088;
(Continued)

(56) References Cited

U.S. PATENT DOCUMENTS 6,846,641 B2 1/2005 Wieloch
6,990,021 B2 1/2006 Pekny
(Continued)

FOREIGN PATENT DOCUMENTS

WO 2004020341 A2 3/2004

OTHER PUBLICATIONS

Moore et al., "Biotechnology and Bioengineering, vol. 103, No. 1, May 1, 2009". (Year: 2009).*
(Continued)

*Primary Examiner* — Liban M Hassan
(74) *Attorney, Agent, or Firm* — MASCHOFF BRENNAN

(57) ABSTRACT

A method of creating a reperfusion injury can include: providing a cell culture device having an internal chamber with at least one port coupled to a perfusion modulating system capable of modulating perfusion in the internal chamber, wherein the internal chamber includes a cell culture; perfusing a fluid through the internal chamber with the perfusion modulating system, wherein the perfusion modulating system includes at least one pump; reducing fluid flow through the internal chamber; reperfusing fluid flow through the internal chamber; and creating a reperfusion injury in the cell culture by the reperfusion of the fluid flow through the internal chamber. The cell culture includes at least one type of tissue cell. The cell culture can include a tissue construct formed of hydrogel and/or extracellular matrix.

21 Claims, 20 Drawing Sheets

Related U.S. Application Data is a division of application No. 14/202,491, filed on Mar. 10, 2014, now abandoned.

(60) Provisional application No. 61/775,158, filed on Mar. 8, 2013.

(52) U.S. Cl.
CPC ..... *G01N 33/5061* (2013.01); *G01N 33/5088* (2013.01); *G01N 33/86* (2013.01); *B01L 3/5027* (2013.01); *G01N 2333/4703* (2013.01); *G01N 2333/70525* (2013.01)

(58) Field of Classification Search
CPC ........... G01N 33/86; G01N 2333/4703; G01N 2333/70525; G01N 33/68; G01N 33/50; G01N 33/84; G01N 2500/10; B01L 3/5027; B01L 2200/0647; B01L 2200/0694; B01L 2300/0645; B01L 3/502746; C40B 30/06
See application file for complete search history.

(56) References Cited

U.S. PATENT DOCUMENTS

| | | |
|---|---|---|
| 7,790,443 B2 | 9/2010 | Wikswo et al. |
| 8,355,876 B2 | 1/2013 | Prabhakarpandian et al. |
| 8,380,443 B2 | 2/2013 | Prabhakarpandian et al. |
| 10,775,364 B2 | 9/2020 | Prabhakarpandian et al. |
| 2002/0160505 A1 | 10/2002 | Groves et al. |
| 2006/0154361 A1 | 7/2006 | Wikswo et al. |
| 2006/0258000 A1 | 11/2006 | Allen |
| 2010/0112690 A1 | 5/2010 | Eddington |
| 2011/0104658 A1 | 5/2011 | Prabhakarpandian et al. |
| 2011/0257504 A1* | 10/2011 | Hendricks ................ A61N 1/05 607/45 |
| 2013/0149735 A1 | 6/2013 | Prabhakarpandian et al. |
| 2014/0255970 A1 | 9/2014 | Prabhakarpandian et al. |
| 2014/0255971 A1 | 9/2014 | Prabhakarpandian et al. |
| 2016/0153970 A1 | 6/2016 | Prabhakarpandian et al. |

OTHER PUBLICATIONS

Giedt, Randy et al., "Free Radical Biology & Medicine 52, 348-356." (Year: 2012).*

Yang, et al., An In Vitro Model Of Ischemic Stroke, Methods in Molecular Biology, vol. 814, pp. 451-466 (2012).

Shevkoplyas et al.; Microvascular Research (2003); vol. 65, pp. 132-136.

Dickerson et al.; Biotechnology and Bioengineering (2001); vol. 73, Issue 6, p. 500-509.

Tan et al.; "Microfluidic Patterning of Cellular Biopolymer Matricies for Biomimetic 3-D Structures"; Biomedical Microdevices (2003); 5(3); 235-244.

Runyon et al.; "Minimal Function Model of Hemostasis in a Biomimetic Microfluidic System"; Angew Chem Int Ed. (2004); 43:1531-1536.

Lim et al.; Fabrication of Microfluidic Mixers and Artificial Vasculatures Using a High-Brightness Diode-Pumped ND: Yag Lader Direct Write Method, Lab Chip; 2003, col. 3, pp. 318-323.

* cited by examiner

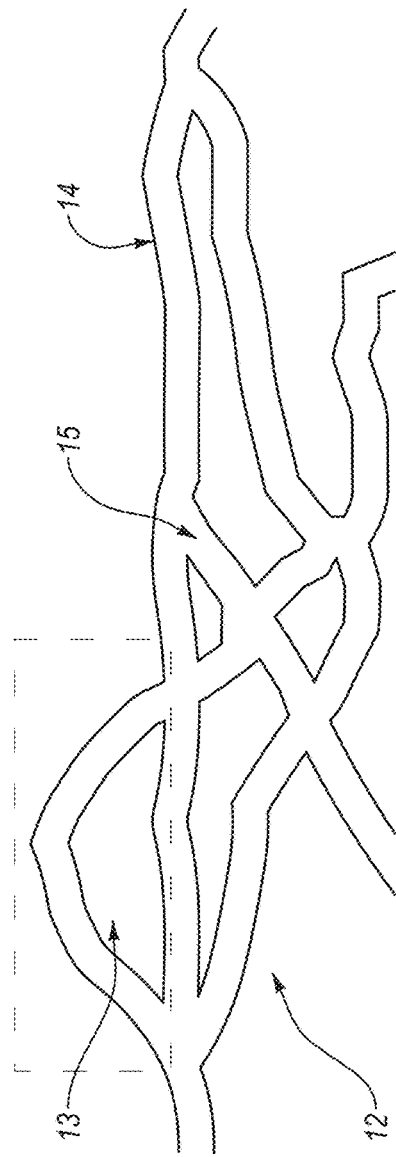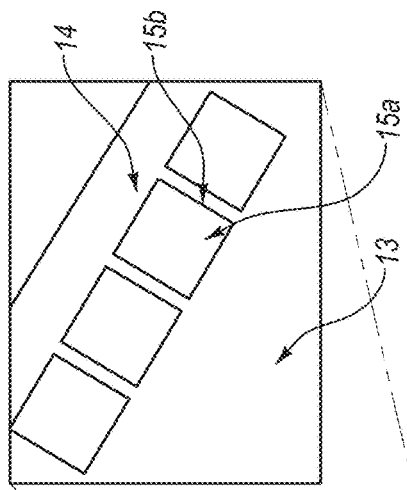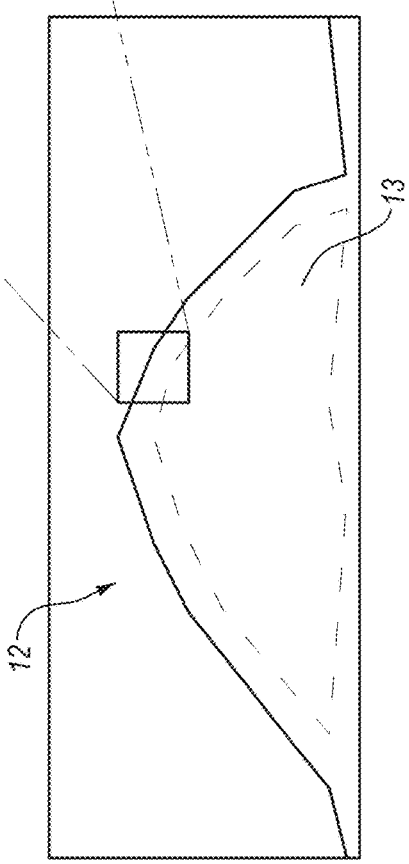
FIG. 2A
FIG. 2B

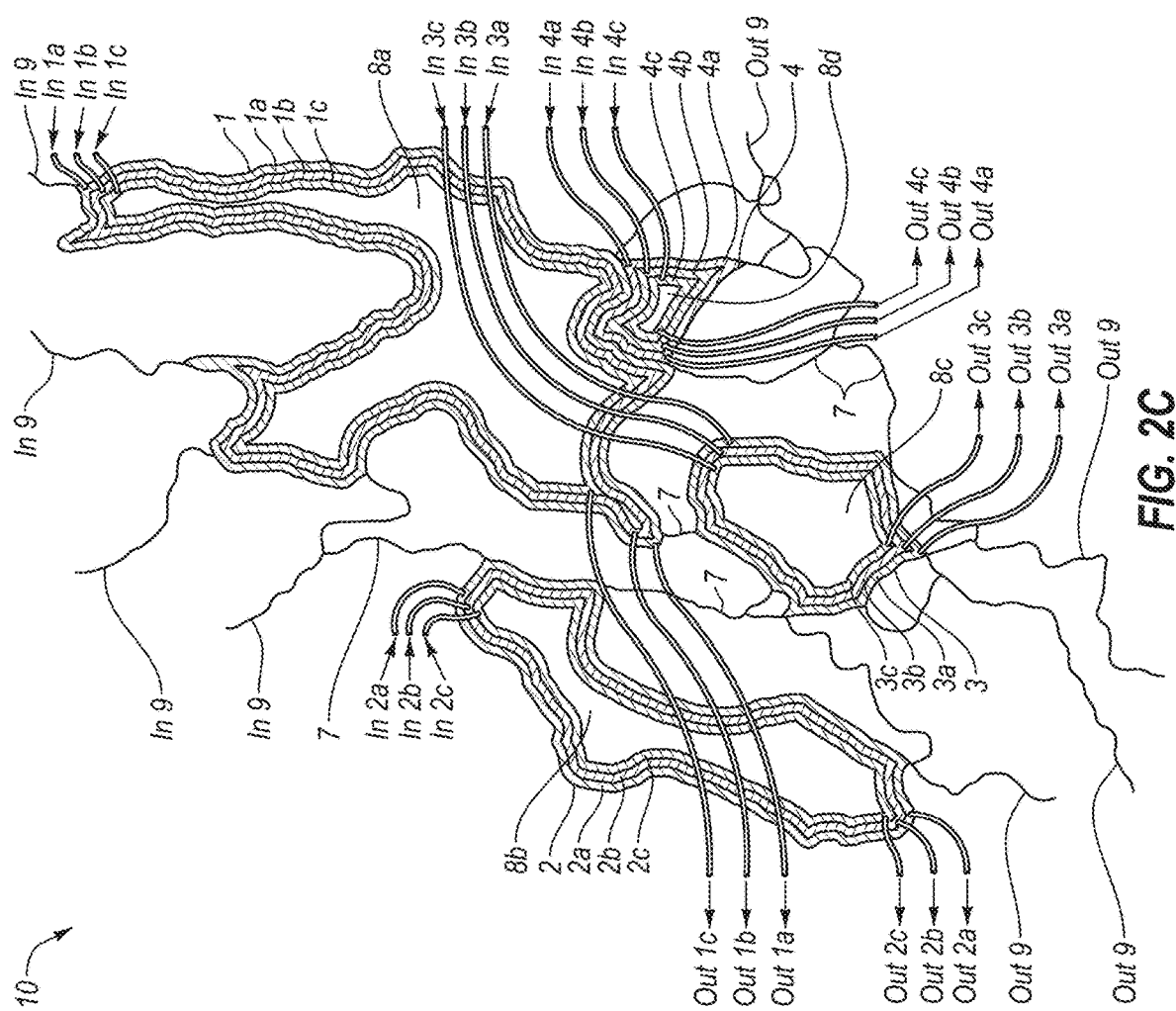

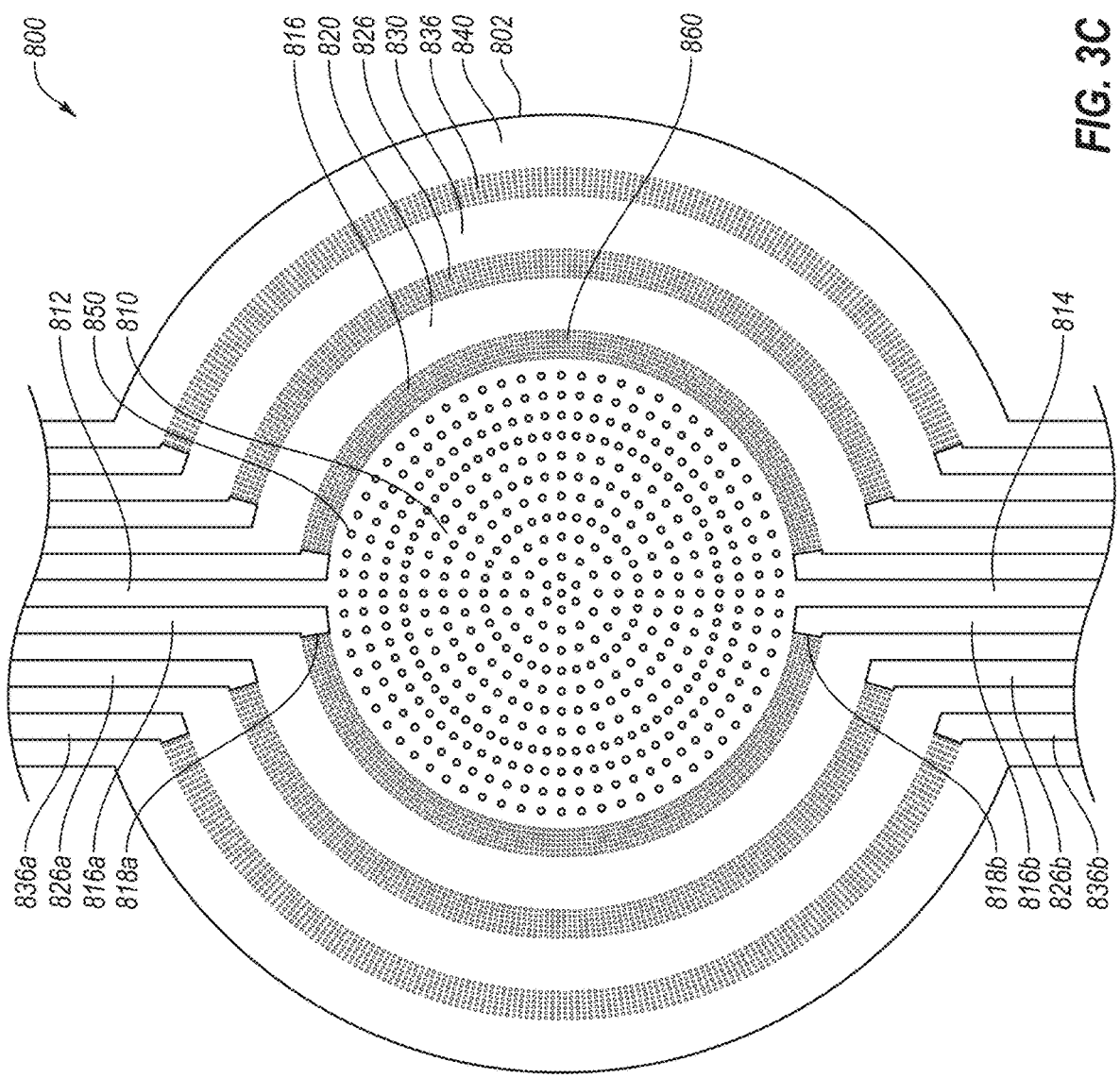

SYSTEMS AND METHODS FOR REPERFUSION INJURY

CROSS-REFERENCE

This patent application is a continuation-in-part of U.S. application Ser. No. 15/017,125 filed Feb. 5, 2016 now U.S. Pat. No. 10,775,364, which is a divisional of U.S. application Ser. No. 14/202,491 filed Mar. 10, 2014 now abandoned, which claims priority to U.S. Provisional Application No. 61/775,158 filed Mar. 8, 2013, which applications are incorporated herein by specific reference in their entirety.

BACKGROUND

Ischemia and hypoxia are common in several pathological conditions, such as cancer, stroke, acute renal failure, and myocardial infarction. Myocardial infarction occurs when the blood supply from a coronary artery is occluded leading to reduced supply (e.g., ischemia) that results in hypoxia to portions of the myocardium. This blockage of the blood flow and oxygen supply is primarily due to an atherosclerosis plaque leading to partial or complete occlusion of the vessel and subsequent myocardial ischemia. Total occlusion of the vessel for more than 4-6 hours results in irreversible myocardial necrosis, but reperfusion within this period can salvage the myocardium and reduce morbidity and mortality. However, reperfusion can create a reperfusion injury. Following an ischemic attack, a series of response mechanisms in the heart, neural, hormonal systems, and vasculature are activated which though initially for beneficial purposes can contribute to worsening of the symptoms and eventual death.

Most of the models of in vivo myocardial ischemia use rodents. In the most commonly used experimental model, the left anterior descending coronary artery commonly called as LADA is ligated. This causes reduction in blood flow and subsequent ischemia. Fluorescent imaging is then used to visualize the vessels. For example, CD31 staining is used to visualize anatomic vessels and DiOC7 is used to visualize perfusion. Finally tissue hypoxia is quantified with EFS, a nitroheterocyclic compound that has been shown to form adducts at a much higher rate in hypoxic tissue. Even though the animal experiments provide detailed representation following ischemia, these experiments are expensive, technically complex and need to overcome ethical concerns.

In this regard, in vitro models were developed to study the effect of ischemia on cultured cardiomyocytes. These models range from treating cells to oxygen deprived media, elevated carbon dioxide levels, reduced nutrient media (absence of serum, etc.), and finally waste accumulation. Common methods rely on altering the cellular metabolism with a chemical agent (e.g., cyanide, azide, Antimycin A, etc.) or altering the external cellular environment by changing gas compositions which is achieved by changes in temperature and rate of change of fresh media. Currently, ischemia studies on myocytes cultured in vitro use one of the following two methods. In the first method, myocytes are cultured in a 35 mm Petri dish. When the cells are nearing confluency, a round glass coverslip is placed over part of the myocyte monolayer surface to restrict nutrient supply and gas diffusion. This rapidly decreases intracellular pH and produces three distinct zones within the monolayer called the ischemic zone (e.g., where the cells don't have access to fresh media and waste metabolites are present in excess), the border zone (e.g., partial cells experience excess waste metabolites and hypoxia whereas the other half of cells are viable), and finally the non-ischemic zone, where the cells have abundant supply of fresh nutrients. A less popular method called the picochamber system can be used to study ischemic conditions on a single cell where the cellular microenvironment oxygen is altered by an argon stream parallel to the surface.

Once reperfusion occurs, the tissues may be injured by the flow from the reperfusion. However, reperfusion injury can cause significant complications in a subject. Ischemia reperfusion injury (IRI) occurs when blood supply, perfusion, and oxygenation is restored to an organ or area following an initial poor blood supply (hypoxia) after a critical time period. The IRI leads to damage across organs including brain, cardiac, kidney, liver and intestine, among others. The IRI results from several complex mechanisms that involve the production of reactive oxygen species (ROS), alterations in intracellular calcium handling, microvascular and endothelial cell dysfunction, altered cellular metabolism, and activation of neutrophils, platelets and complement. The ROS are considered key molecules in reperfusion injury due to their potent oxidizing and reducing effects that directly damage cellular membranes. ROS also activate endothelial cells elevating adhesion molecules that play a major role in the interactions between the neutrophil and the endothelium. Major ROS involved in an IRI include superoxide anion, hydrogen peroxide, hydroxyl radical, nitric oxide and peroxynitrite. Other contributors for IRI include eicosanoids comprising of prostaglandins, thromboxanes and leukotrienes. Additional molecules that lead to the IRI are nitric oxide, endothelin, cytokines, complement activation factors and proteases.

Therefore, it would be advantageous to have devices and methods that provide for improved experimental analysis and studies on cells and cultures that experience reperfusion and reperfusion injury.

SUMMARY

In some embodiments, a method of creating a reperfusion injury can include: providing a cell culture device having an internal chamber with at least one port coupled to a perfusion modulating system capable of modulating perfusion in the internal chamber, wherein the internal chamber includes a cell culture; perfusing a fluid through the internal chamber with the perfusion modulating system, wherein the perfusion modulating system includes at least one pump; reducing fluid flow through the internal chamber; reperfusing fluid flow through the internal chamber; and creating a reperfusion injury in the cell culture by the reperfusion of the fluid flow through the internal chamber.

In some embodiments, the cell culture includes at least one type of tissue cells. In some aspects, the at least one type of tissue cells includes myocytes, neurons, nephrons, and hepatocytes. In some aspects, the cell culture includes cells from organs including brain, cardiac, kidney, liver and intestine, among others.

In some embodiments, the fluid includes a liquid carrier having oxygen. In some aspects, the method can include varying intensity of perfusion or duration of perfusion by changing flow rate of the fluid, which can be done with the pumps and/or valves of the perfusion modulating system. In some aspects, the method can include creating hypoxia in the cell culture from the reduced fluid flow, such as under control of a controller operating the pumps and/or valves. In some aspects, the method can include occluding fluid flow prior to the reperfusing, such as with the pump switching off or switching the valves closed.

In some embodiments, the method can include determining an effect of the reperfusion on the cell culture based on the reperfusion injury. Such an effect can be determined by performing an assay to measure a parameter of the cell culture, such as those described herein. In some aspects, the method can include monitoring the cell culture with electrodes in the internal chamber, such as to measure a parameter of the cell culture and changes of the parameter after a reperfusion injury. In some aspects, the method can include performing impedance measurements (e.g., with electrodes) on the cell culture. In some aspects, the method can include assessing damage of the cell culture from the reperfusing by determining: changes in pH, upregulation of inflammation markers, increase in reactive oxygen species, changes in intracellular calcium, microvascular dysfunction, epithelial cell dysfunction, altered cellular metabolism, activation of neutrophils, activation of platelets, activation of complement factors and proteases, increase in eicosanoids, increase in nitric oxide, increase in endothelin, increase in cytokines, or viability of cells of the cell culture.

In some embodiments, the method can include: at least one fluid channel bordering the internal chamber of the cell culture device; and at least one wall separating the internal chamber and the at least one fluid channel, wherein the at least one wall includes at least one gap, each gap fluidly coupling the internal chamber with the at least one fluid channel. In some aspects, the perfusion modulating system is fluidly coupled to at least one port in the cell culture device. In some aspects, the port in the cell culture device is in at least one fluid channel that borders the internal chamber. In some aspects, the port in the cell culture device is in the internal chamber.

In some embodiments, the method can include monitoring the cell culture during the steps of perfusing fluid flow through the internal chamber, reducing fluid flow through the internal chamber, and reperfusing fluid flow through the internal chamber.

In some embodiments, the methods can include: introducing a test substance to the internal chamber before, during or after the reperfusion injury; and screening the cell culture for changes in response to the test substance (e.g., after a reperfusion injury). In some aspects, the method can include determining a mechanism of action of the test substance on the cell culture based on the changes in response to the test substance.

In some embodiments, the cell culture device can include one or more electrodes associated with the internal chamber, fluid channel, and/or tissue construct. In some aspects, the electrodes are 2D electrodes or 3D electrodes.

In some embodiments, the cell culture includes a tissue construct composed of a porous 3D matrix. The porous 3D matrix can be formed of hydrogels and/or extracellular matrix. The tissue construct can include hydrogels or porous scaffolds composed of synthetic polymers, such as polyethylene glycol (PEG), polyethylene glycol diacrylate (PEGDA), polycaprolactone (PCL), polyvinyl alcohol (PVA), poly(d,l-lactide-co glycolide) (PLGA), or the like. The tissue construct can also be a porous 3D matrix of native or modified extracellular matrices, such as collagen, collagen methacrylate (ColMA), gelatin, gelatin methacrylate (GelMA), chitosan, alginate, silk, elastin, laminin, fibronectin, hyaluronic acid, and the like. The tissue construct can utilize either individual or mixtures of these components for supporting cell culturing and tissue formation. In some aspects, the tissue construct includes: one or more three-dimensional electrodes inserted into the tissue construct; and/or one or more fluid flow channels passing through the tissue construct, the one or more fluid flow channels including one or more apertures to allow for perfusion of the fluid into the tissue construct.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 2A illustrates an embodiment of a cell culture device having a plurality of internal chambers and fluid channels that are modeled from physiological features.

FIG. 2B illustrates a magnification of a wall separating the internal chamber and fluid channels.

FIG. 2C illustrates an embodiment of a cell culture device having multiple channels.

FIG. 3C illustrates an embodiment of a circular cell culture device having an internal chamber and multiple fluid channels that are idealized.

DETAILED DESCRIPTION

Figure 1A:
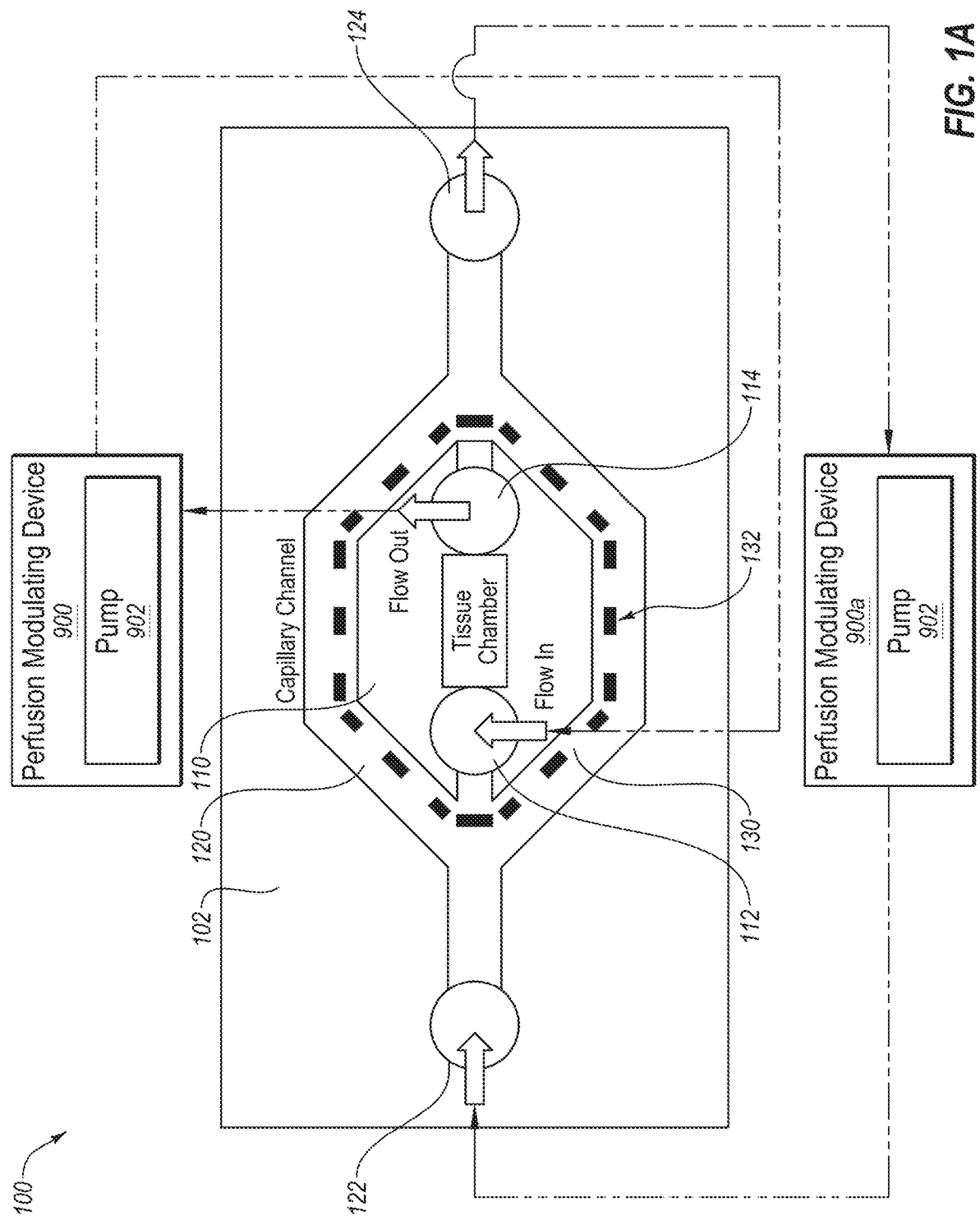
FIG. 1A illustrates an embodiment of a cell culture device for use in ischemia, hypoxia, and reperfusion assays.

In the following detailed description, reference is made to the accompanying drawings, which form a part hereof In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention includes a microfluidic device and assay for studying ischemia, hypoxia, and reperfusion injury on cells in controlled perfusion, flow occlusion, and reperfusion conditions. The microfluidic device can induce ischemia and hypoxia by interrupting the flow of media and oxygen to cells in the microfluidic device. The device can be operably coupled with a perfusion modulating system that can selectively block the flow of oxygen or fluids having oxygen (e.g., cell culture media) from the cells in the device, which simulates blocking blood in vessels from supplying oxygen to tissue to provide a hypoxic condition. The resulting restriction of flow causes an oxygen shortage in the cells in the device, which can lead to necrosis in portions of the cells, cell culture, or tissue area in the device. The device can be used for a controlled study of ischemia and hypoxia and the impact on cells in the device, which can be extrapolated for understanding ischemia and hypoxia. The device can also be used for development of new therapeutics for treating ischemia and hypoxia affected tissues in a subject. The perfusion modulating system can also be used for reperfusion after the fluid flow occlusion event. The reperfusion can result in a reperfusion injury, which can be studied to understand how reperfusion injury can contribute to problems associated with flow blockage, hypoxia, and ischemia.

The device can be configured for high throughput assays used for studying any type of tissue cell having ischemia or hypoxia or reperfusion injury. The device can have physiological realistic features, such as tissue chambers and vessel flow paths, which can be referred to as a synthetic microvascular network (SMN). The device can have idealistic features, such as straight flow paths and regular shaped tissue chambers, which can be referred to as an idealized microvascular network. SMN and IMN are known terms in the art.

For example, the device can provide a platform for studying myocardial ischemia (MI) in a physiological microenvironment (e.g., SMN environment). MI occurs when the blood supply to portions of the heart is interrupted, which can be simulated by interrupting the flow of cell culture media, oxygen or oxygen-containing fluid to the cells in the device. The device may include means (e.g., perfusion modulating system) for inhibiting the supply of media and/or oxygen to the cells, and then introducing reperfusion to the cells. For example, the device can be used to simulate blockage of a coronary artery following the rupture of an atherosclerotic plaque by reducing or stopping fluid flow to the chambers of the device, and simulate reperfusion by reintroducing fluid flow to the chambers of the device. The reduced flow of media (e.g., simulated blood supply) can simulate ischemia, and the nutrient shortage can lead to myocardial necrosis, which can cause contractile dysfunction and hinder the ability of the heart to perfuse vital organs necessary for survival. The same technique can be used to inhibit oxygen and induce hypoxia in the cell cultures of the device that are from various organs, such as by the cell culture including cells from organs including brain, cardiac, kidney, liver and intestine, among others. The examples presented here is based on myocytes. However, the device can use other cells to study ischemia and hypoxia in other tissues, such as those cells described herein. After inhibiting oxygen through inhibiting fluid flow, the device can reintroduce fluid flow into the cell culture chambers by reperfusion from the perfusion modulating system, which reperfusion can cause a reperfusion injury.

The device can be configured to provide an in vitro model to reproduce as many anatomical, physiological and biochemical aspects as possible of the in vivo features, in order to be functional and accurate. As such, the device can include a microenvironment with an internal chamber having myocytes, neurons, nephrons, hepatocytes or other cells surrounded by a network of capillary channels (e.g., having endothelial cells) in the device for providing nutrients to the internal chamber. The shape of the internal chamber and capillary network can be shaped similar to anatomical examples, which can be irregular and non-linear and referred to as synthetic microvascular networks (SMN). Alternatively, the shape of the internal chamber and capillary network can be shaped in an idealized format with straight channels with regular and linear features, which is referred to as an idealized microvascular network (IMN). As such, the microfluidic device can be configured to mimic the microenvironment of tissue cells in a complex network of capillaries. Fluid flow (e.g., simulated blood flow and/or oxygen flow) in these capillary channels surrounding the internal chamber can be readily switched on and off (e.g., with a pump of the perfusion modulating system) to simulate ischemia induced conditions and hypoxia as well as reperfusion and any resulting reperfusion injury. Cultured endothelial cells in the capillaries surrounding the internal chamber (e.g., myocyte culture) enable studies on interaction between endothelial cells and tissue (e.g., myocardium). However, other cells can be used besides myocytes for studying other tissue types.

FIG. 1A illustrates a schematic representation of an embodiment of a microfluidic device 100 in accordance with the present invention. As shown, the device includes a body 102 that defines an internal chamber 110 surrounded by a capillary channel 120. The internal chamber 110 has a flow inlet 112 and a flow outlet 114. The capillary channel 120 has a capillary inlet 122 and a capillary outlet 124. The internal chamber 110 and capillary channel 120 are separated by posts 130 with gaps 132 between the posts 130 to create a porous wall.

The device 100 can include a perfusion modulating device 900 that is shown to include a pump 902, but may include a plurality of pumps. The perfusion modulating device 900 is operably coupled with the flow inlet 112 and flow outlet 114 of the internal chamber 110. Another perfusion modulating device 900a is shown to include a pump 902, but may include a plurality of pumps. The perfusion modulating device 900a is operably coupled with the capillary inlet 122 and capillary outlet 114 of the capillary channel 120.

The capillary channel 120 can be a fluid flow channel and the internal chamber 110 can be a tissue space. The capillary channel 120 and internal chamber can be linear elements or idealized (IMN) or non-linear elements or synthetic (SMN). FIG. 1A illustrates an IMN. The perfusion modulating devices 900 and 900a can be part of a perfusion modulating system, which can include a computer controller.

In one embodiment as shown in FIG. 1A, a cell culture device can include: an internal chamber 110 configured for an internal cell culture that has at least one port (e.g., flow inlet 112 and flow outlet 114) coupled to a perfusion modulating device 900 capable of modulating perfusion in the internal chamber 110; at least one fluid channel (e.g., capillary channel 120) bordering the internal chamber 110 that is configured for a channel cell culture that has at least one port (e.g., capillary inlet 122 and capillary outlet 124) coupled to a perfusion modulating device 900a capable of modulating perfusion in the fluid channel; and a wall (e.g., posts 130 and gaps 132) separating the internal chamber 110 and at least one fluid channel having gaps 132 that fluidly couple the internal chamber 110 with the at least one fluid channel, wherein the perfusion modulating device 900a causes reduced fluid flow. In one aspect, the perfusion modulating device 900, 900a includes a pump 902. In one aspect, the internal chamber 110 includes a first cell type and the at least one fluid channel includes a second cell type. In one aspect, the first cell type has an ischemic zone in the middle, a non-ischemic zone adjacent with the at least one fluid channel, and a border zone between the ischemic zone and non-ischemic zone. In one aspect, the internal chamber 110 and at least one fluid channel 120 are modeled from physiological features. In one aspect, the internal chamber 110 and at least one fluid channel 120 are modeled from idealized features.

Some embodiments of a synthetic microvascular network (SMN) 12 can include realistic flow paths and tissue spaces, as shown in FIG. 2A-2B. The capillary network is irregular. Here, the wall of a flow channel (e.g., capillary channel) separating the flow channel lumen from the lumen of the tissue space 13 is shown in detail to show the pillars 15a and gaps 15b. In this embodiment, one wall of the nonlinear flow channel 14 is constructed such that portions of the wall contain gaps 15b located between portions of the wall, called pillars 15a (or posts, islands, etc.), which may be configured to provide gaps 15b of various selected sizes. For fabrication of the SMN 12 comprising the extravascular (extra-flow channel) tissue space 13, CAD drawings of a physiological network are modified to include gaps 15b with desired gaps or pores in the walls of the vessels. The patterns of these vessels include tissue sections comprising a portion of or the entire physiological tissue space 13. The lumens of the tissue spaces 13 shown in FIGS. 2A and 2B may comprise posts, pillars, or other structures made of plastic substrate to facilitate the growth of adhesion-dependent cells. The non-linear flow channel can be coupled to an inlet and an outlet, which inlet and outlet can be coupled with a perfusion modulating device.

Figure 6:
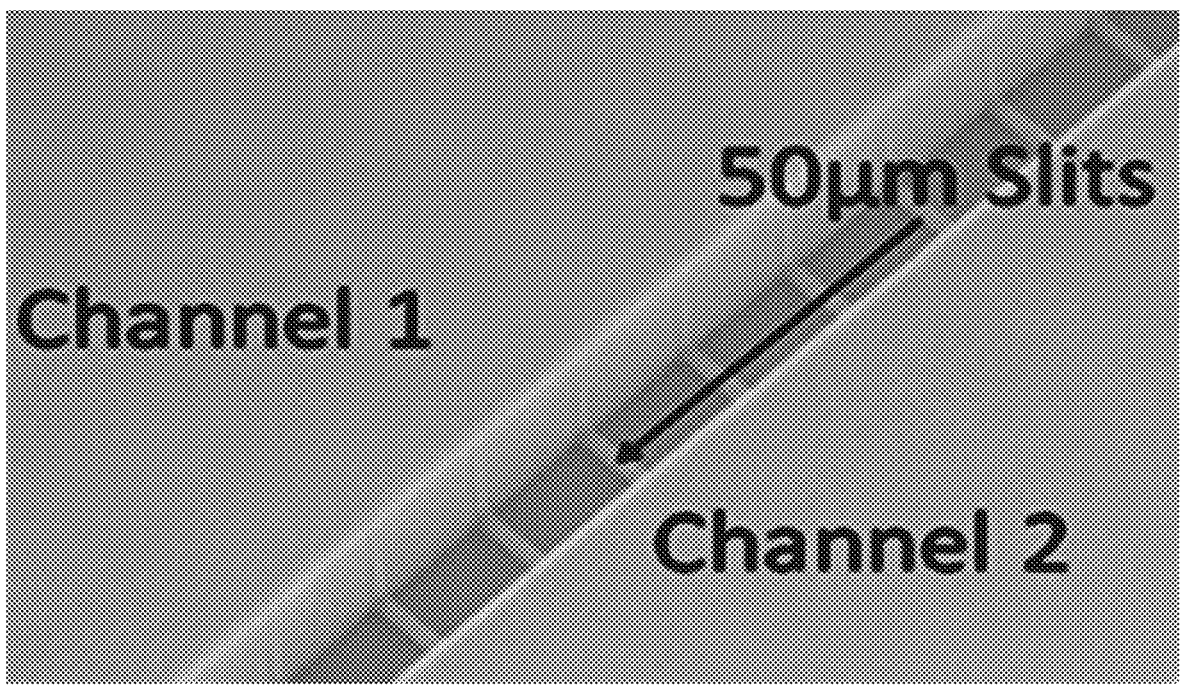
FIG. 6 illustrates an embodiment of a wall with slits that can separate two different channels in the cell culture device.

FIG. 6 shows that two capillary channels can be separated by a wall having 50 micron-wide slits. As such, the devices can include internal chambers surrounded by at least two adjacent capillary channels. In view of the SMN of FIGS. 2A and 2B, a corresponding SMN modeled after live physiology with at least two capillary channels would look like FIG. 2C. FIG. 2C illustrates an embodiment of SMN network having SMN fluid pathways and SMN multi-chambered cell culture constructs.

FIG. 2C illustrates a SMN 10 having one of more fluid inlets In 9 and one or more fluid outlets Out 9 with one or more multi-channel constructs 1, 2, 3, 4, each having a central chamber 8a, 8b, 8c, 8d (e.g., while four multi-chamber constructs are shown, any integer can be used). The multi-chamber constructs 1, 2, 3, 4 can be configured with inlets and outlets in accordance with any of the embodiments or figures described herein. Also, while shown to be SMN, the configuration can be an IMN. The SMN can be configured with any number of fluid pathways 7 linking the multi-channel constructs, which can be in any manner, and which SMN can be designed via simulation of real biological or artificial fluid pathways.

As shown, multi-channel construct 1 can include a central chamber 8a surrounded by an outer conduit layer 1a (e.g., outer capillary channel) with barrier layer channels 1b, 1c therebetween. The outer conduit layer 1a can be fluidly coupled with an inlet In 9 and an outlet Out 9. Also, the outer conduit layer 1a can include an inlet In 1a and an outlet Out 1a. The barrier layer channels 1b, 1c, can include inlets In 1b, In 1c and outlets Out 1b, Out 1c, respectively. While not shown, the central chamber 8a can include inlets or outlets, or it can receive content from the barrier layer channel 1c.

As shown, multi-channel construct 2 can include a central chamber 8b surrounded by an outer conduit layer 2a (e.g., capillary channel) with barrier layer channels 2b, 2c therebetween. The outer conduit layer 2a can be fluidly coupled with an inlet In 9 and an outlet Out 9. Also, the outer conduit layer 2a can include an inlet In 2a and an outlet Out 2a. The barrier layer channels 2b, 2c, can include inlets In 2b, In 2c and outlets Out 2b, Out 2c, respectively. While not shown, the central chamber 8b can include inlets or outlets, or it can receive content from the barrier layer channel 2c.

As shown, multi-channel construct 3 can include a central chamber 8c surrounded by an outer conduit layer 3a (e.g., outer capillary channel) with barrier layer channels 3b, 3c therebetween. The outer conduit layer 3a can be fluidly coupled with an inlet In 9 and an outlet Out 9. Also, the outer conduit layer 3a can include an inlet In 3a and an outlet Out 3a. The barrier layer channels 3b, 3c, can include inlets In 3b, In 3c and outlets Out 3b, Out 3c, respectively. While not shown, the central chamber 8a can include inlets or outlets, or it can receive content from the barrier layer channel 3c.

As shown, multi-channel construct 4 can include a central chamber 8d surrounded by an outer conduit layer 4a with barrier layer channels 4b, 4c therebetween. The outer conduit layer 4a can be fluidly coupled with an inlet In 9 and an outlet Out 9. Also, the outer conduit layer 4a can include an inlet In 4a and an outlet Out 4a. The barrier layer channels 4b, 4c, can include inlets In 4b, In 4c and outlets Out 4b, Out 4c, respectively. While not shown, the central chamber 8d can include inlets or outlets, or it can receive content from the barrier layer channel 4c.

Each inlet and outlet can be coupled to a perfusion modulating system, where each inlet and/or outlet pair can be coupled with an individual pump of the perfusion modulating system.

Figure 3A:
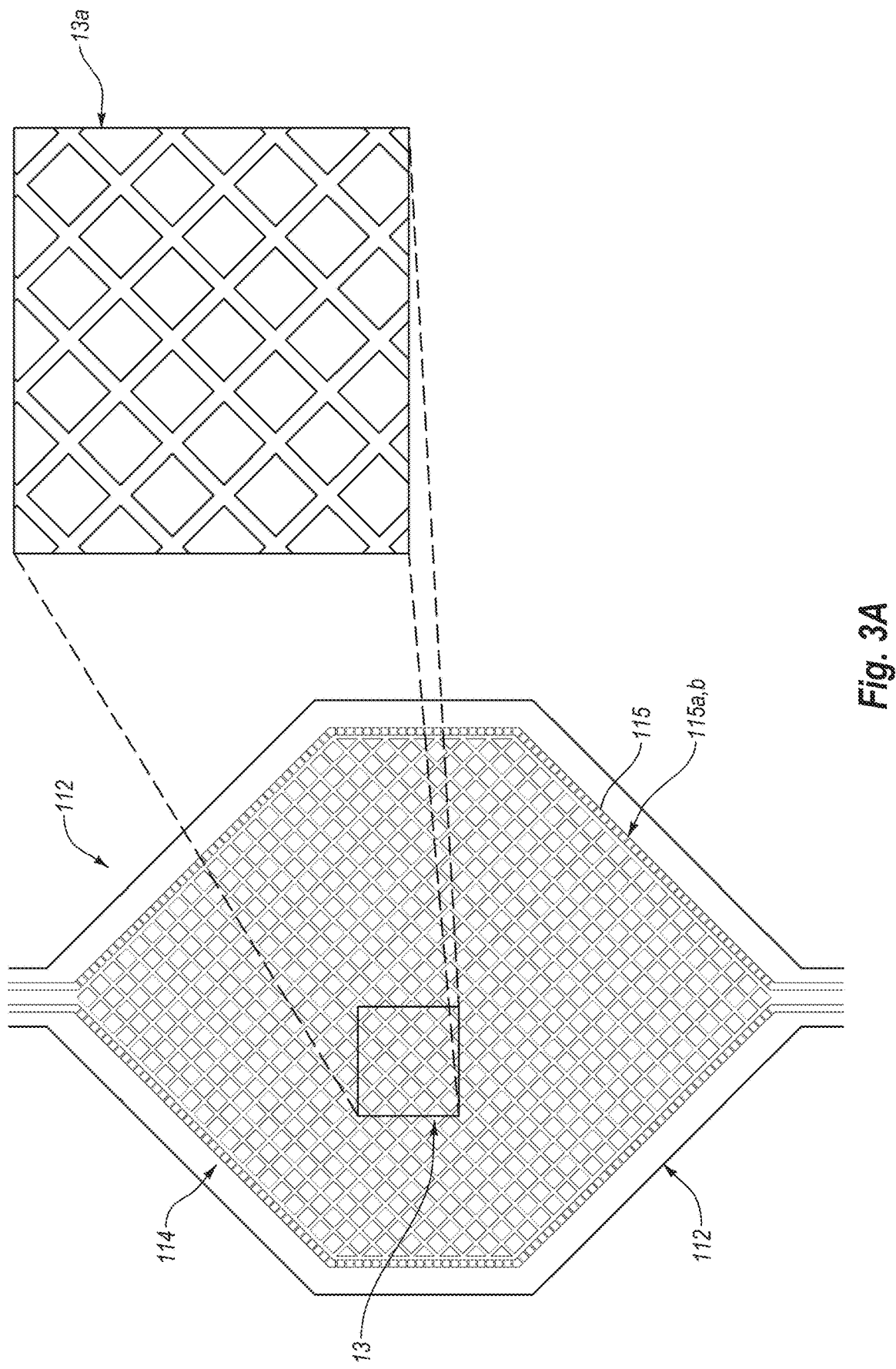
FIG. 3A illustrates an embodiment of an idealized cell culture device having an internal chamber and fluid channels that are idealized.

FIG. 3A shows a portion of an idealized microvascular network IMN 112 in a microfluidic chip. The IMN 112 comprises the idealized extravascular tissue space 13 surrounded by linear flow channels 114. Walls 115 separating the tissue space 13 from the linear flow channels 114 are permeable to aqueous buffers and are formed by plastic structures 115b separated by gaps 115a that range in size from 0.2 µm to 5 µm. Alternatively, the walls 115 may be made liquid permeable by way of pores in the wall that are from 0.2 µm to 30 µm in diameter. The extravascular tissue space 13 contains posts 13a (e.g., pillars) configured to facilitate the growth of adhesion-dependent cells to form a three-dimensional solid mono- or co-tissue culture or tumor. The posts 13a can be included in any vascular fluid flow path or extravascular space in any of the microfluidic chips. The posts 13a distribution, amount or arrangement or shape. Also, the tissue space 13 can be devoid of the posts 13a. The idealized extravascular tissue space 13 is shown to have an inlet and outlet at the ends, which can be coupled with the perfusion modulating system. Also, the linear flow channels 114 each include an inlet and outlet that can be coupled with the perfusion modulating system.

Figure 3B:
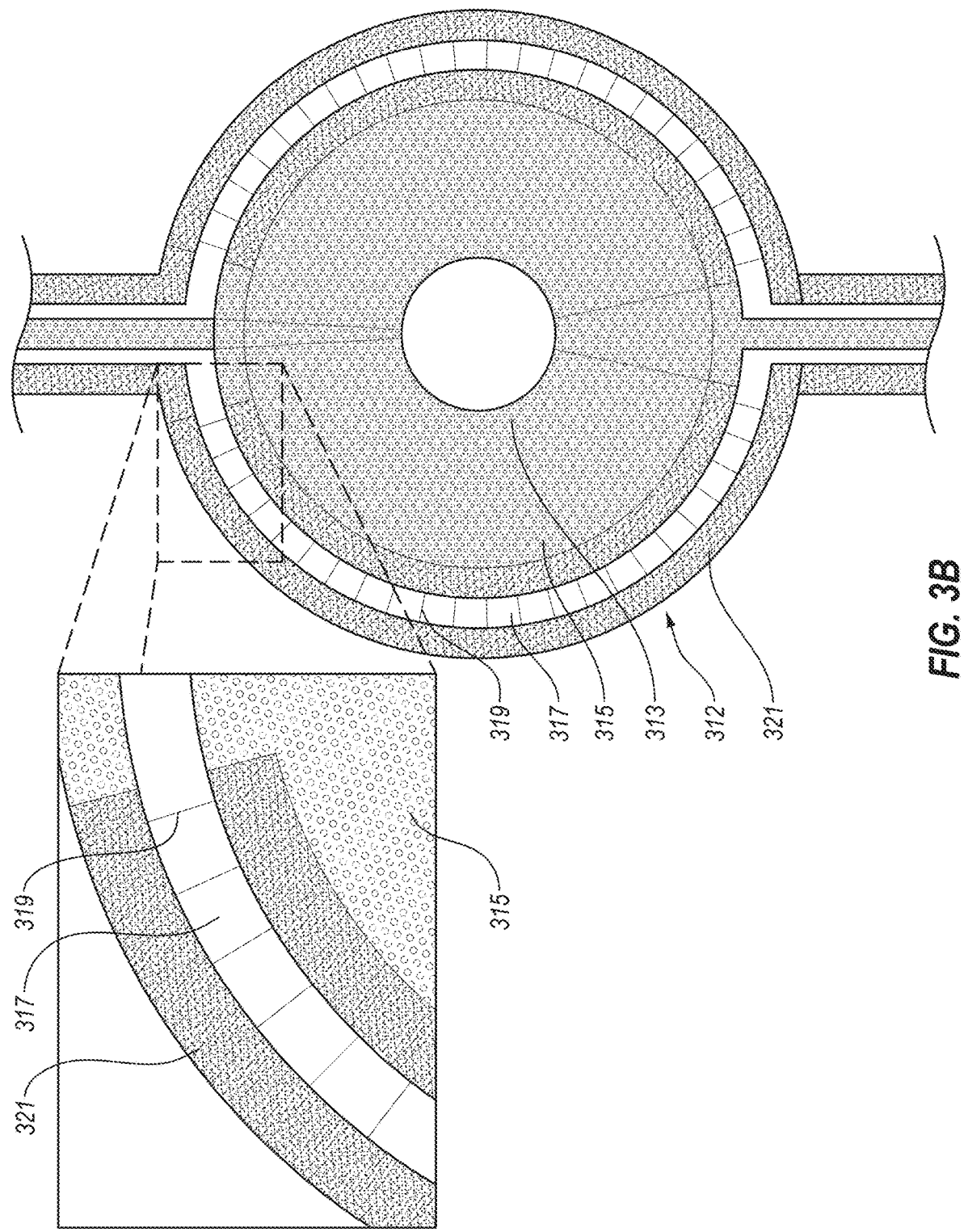
FIG. 3B illustrates an embodiment of a circular cell culture device having an internal chamber and fluid channels that are idealized.

FIG. 3B shows a round IMN 312 in a microfluidic chip. The IMN includes a round tissue space 313 surrounded by a barrier space 315, which is surrounded by a wall 317 having gaps 319, and where an outer capillary channel 321 is on the outside. As shown, the barrier space 315 can include posts or pillars for cell culturing tissue. Here, the round tissue space 313 is shown to include an inlet and an outlet on opposite sides thereof, which inlet and outlet can be coupled with a pump of the perfusion modulating system. Also, the outer capillary channels 321 each include an inlet and an outlet on opposite sides thereof, which inlet and outlet for each channel can be coupled to an individual pump or valve of the perfusion modulating system. Thus, the prefusion modulating system can include a pump and/or valve for each channel or each chamber.

The embodiments of the device can include a plastic, disposable and optically clear microfluidic chip containing two distinct sections. The first section includes an internal chamber for culture of tissue cells surrounded by the second section being capillaries of endothelial cells. The device can be created by separating the internal chamber (e.g., tissue chamber) for culture of cells (e.g., tissue being studied) from the capillary channels lined with endothelial cells by utilizing posts that mimic membranes. The posts create islands which are separated by submicron-micron gaps to allow for diffusion based fluidic connection between the capillary channels and the central chamber leading to a microenvironment observed in vivo with cells being surrounded by capillaries.

Figure 5:
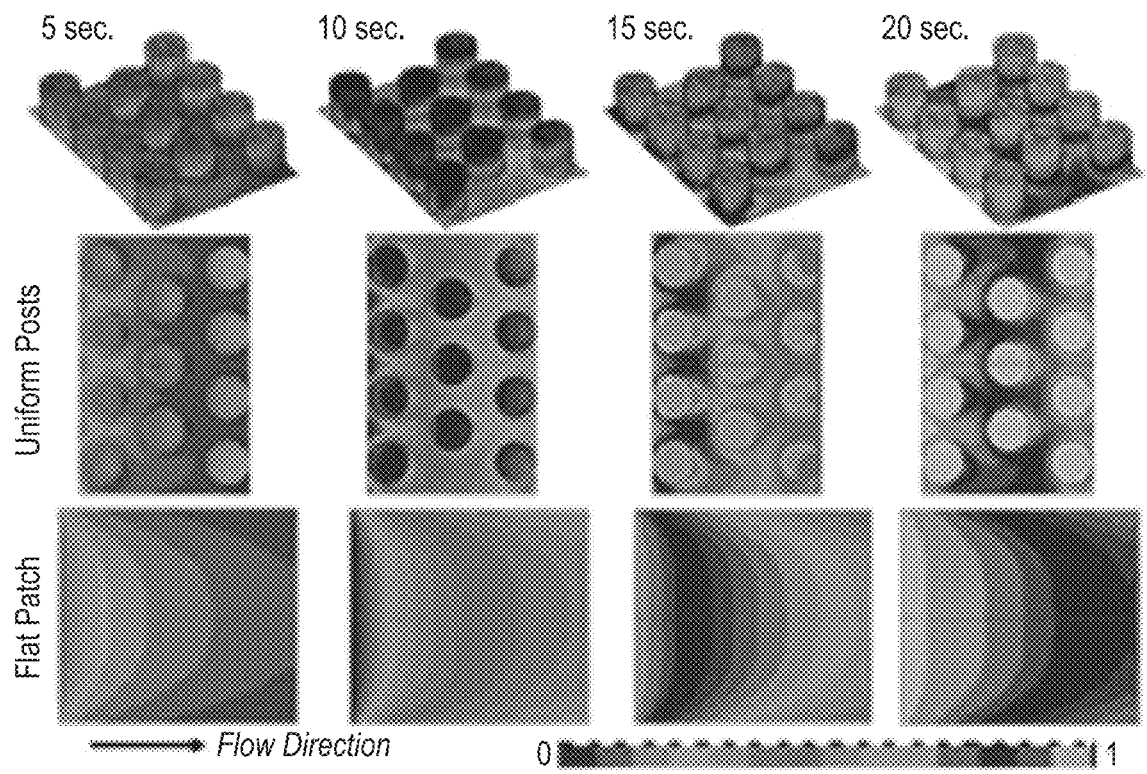
FIG. 5 illustrates fluid flow dynamics with posts that can be used as walls between the internal chamber and channels.

FIG. 5 shows that multiple pillars be used in the flow direction, which is from the capillary channels into the central chamber. As such, the walls can be a series of pillars with gaps and flow space therebetween.

FIG. 3C shows another embodiment of a multi-channel structure 800 in accordance with the principles of the present invention. Here, the walls are made of the series of pillars in accordance with FIG. 5. The multi-channel cell culture device 800 is shown to include an internal chamber 810, an inner boundary layer channel 820, an outer boundary layer channel 830, and an outer conduit layer channel 840. However, only one boundary layer channel or more than two additional boundary layer channels can be located between the internal chamber 810 and outer conduit layer channel 840. The internal chamber 810 can include a fluid inlet 812 and a fluid outlet 814, which can be fluidly coupled with the perfusion modulating system. The inner boundary layer channel 820 can include at least one fluid inlet and at least one fluid outlet as described herein, which can be coupled with its own pump of the perfusion modulating system. The outer boundary layer channel 830 can include at least one fluid inlet and at least one fluid outlet as described herein, which can be coupled with its own pump of the perfusion modulating system. The outer conduit layer channel 840 can include at least one fluid inlet and at least one fluid outlet as described herein, which can be coupled with its own pump of the perfusion modulating system. The internal chamber 810 can be defined by a porous tissue chamber wall 816, the inner boundary layer channel 820 can be defined by the porous tissue chamber wall 816 and a porous boundary layer wall 826, the outer boundary layer channel 830 can be defined by the porous boundary layer wall 826 and a porous outer conduit wall 836, and the outer conduit layer channel 840 is defined by the porous outer conduit wall 836 and an external wall 802 that is not porous. Here, the porous walls 816, 826, 836 can include a plurality of posts 860 that form the walls with the gaps between the posts 860. The porous walls 816, 826, 836 have one or more posts 860 laterally or radially oriented to form the walls.

In one embodiment, any of the chambers/conduits can include structure posts 850 that can be used to provide structure between top walls and bottom walls. The structure posts 850 can be coupled to a bottom wall, and may be coupled to a top wall when integrated with the side walls. Also, the top wall as a lid can rest on the structure posts 850. The structure posts can be used for cell culture, and can result in a higher cell density for organ simulations. FIG. 3C shows the central chamber 810 as having the posts 850, but it can be devoid of posts. Any of the boundary channels 820, 830 can include the posts 850 or be devoid of posts. The outer channel 840 can include the posts 850 or be devoid of posts The device having the internal chamber surrounded by the capillary channels accurately reproduces the size and flow of a biological microenvironment, and enables a more physiologically-relevant testing system for therapeutic screening, as well as basic research of ischemia, hypoxia and reperfusion injury. Advantages in microfluidic technology (e.g., polydimethylsiloxane or PDMS based device) enable creation of small volume, inexpensive, disposable chips having the internal chamber surrounded by the capillary channels. Very thin (e.g., <100 µm) PDMS constructs can be used to realize long-term cell culture and cellular assays on these microfluidic chips. In one example, by bonding the polymer microchannel to a custom glass bottom laid out in the appropriate form, the model can be readily extended onto standard well plates (e.g., 24 well plates), providing a ready method to scale-up to high-throughput screening. The device configuration provides the ability to study differences between healthy and diseased microvasculature of the cells (e.g., study tissue), such as before and after a reperfusion injury. The internal chamber and channels can be connected to a perfusion modulating system, such as shown in the figures herein (e.g., pumps and/or valves with the inlets and outlets).

In one embodiment, the device can provide a microenvironment (e.g., size, volume, and vasculature) of the cells (e.g., study tissue) with a network of endothelial cells in the capillary channels surrounding the cells in the internal chamber. The device configuration allows perfusion, occlusion, and reperfusion at the flow rates observed in live capillaries by application to the channels of the device. The reperfusion can be induced at flow rates that are biological or artificial to create the reperfusion injury. The device configuration allows introduction of various insults, chemical (e.g., test pharmaceuticals) or physical (e.g., ischemia and hypoxia or reperfusion) to the cells in the capillary channels and internal chamber. The devices, when made from a transparent material or other optically transmissive material, allows for real-time visualization of the assays. The device is amenable to high throughput for therapeutic screening assays for agents to treat ischemia and hypoxia. Also, electrodes can be introduced into the channels or internal chamber for monitoring the cells of the cell cultures.

Figure 4:
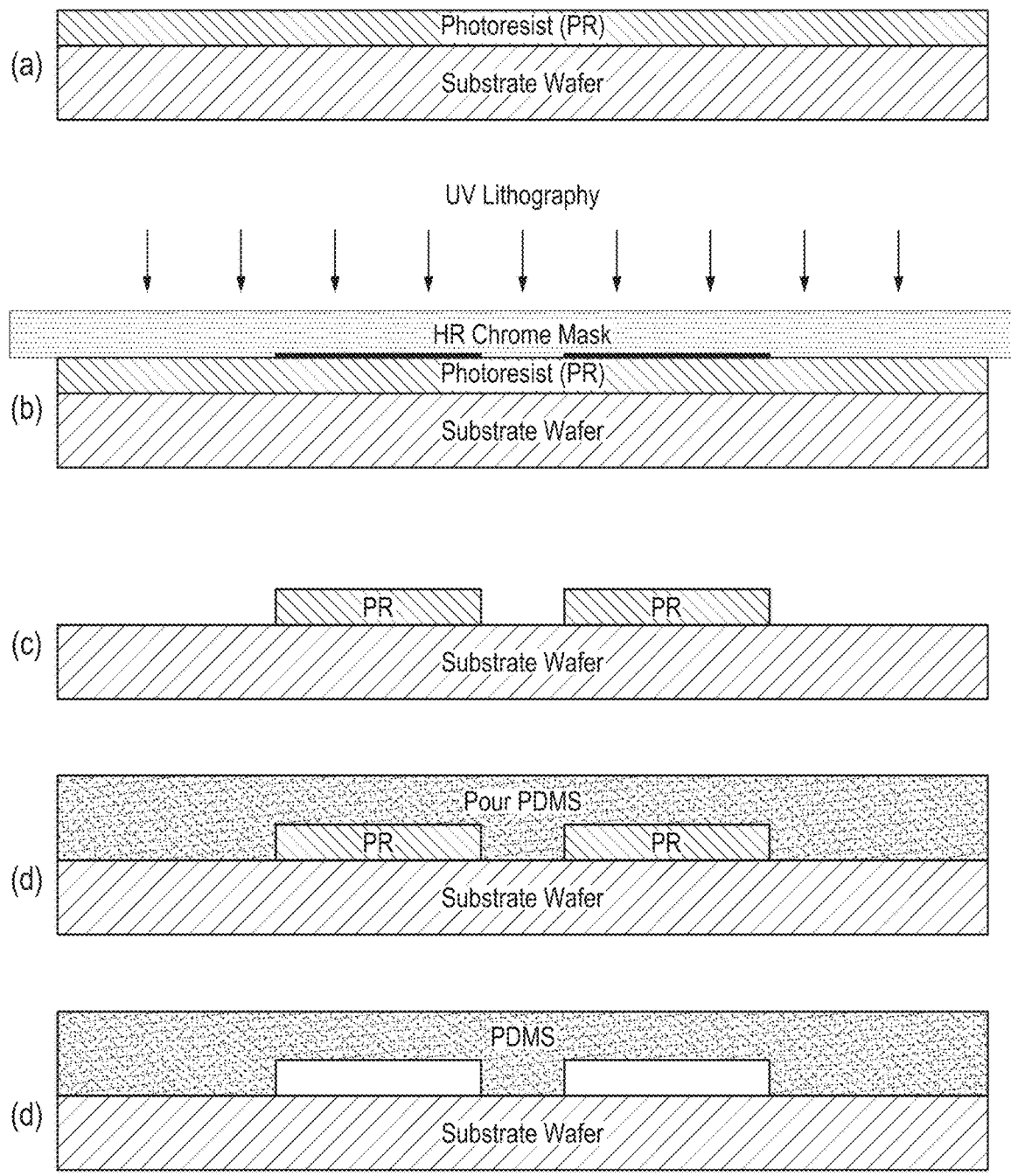
FIG. 4 illustrates an embodiment of manufacturing the cell culture device.

The device can be fabricated with PDMS using conventional soft lithography (see FIG. 4). CAD drawings of the device can be developed to include post structures with gaps to act as paths for diffusion of fluid (e.g., nutrients or oxygen) into the central cell chamber. The CAD drawings can also be converted into a computational domain for simulational analysis. Briefly, the steps involved in the fabrication process shown in FIG. 4 include: (a) Spin-coating of photoresist (PR); (b) UV photolithography of the PR; (c) Development of the PR; (d) PDMS casting over developed PR, followed by PDMS curing; and (e) PDMS bonding to a cap (e.g., microscope slides, coverslip, glass, etc.). The devices can be tested visually for structural and fluidic integrity using fluorescent dyes. Fabrication of microfluidic devices from PDMS can be modulated to vary the widths, depths, PDMS concentration and baking time.

Additional methods can be used for preparing the devices, such as the following example. The AutoCAD designs can be printed at high resolution on high-quality chrome masks. The chrome masks can be used for UV patterning of the desired thickness of positive resist spun on top of a silicon wafer. Silanization via the use of an adhesion promoter (Hexamethyldisilazane, HMDS) can be used to enhance the strength of bonding of the photoresist to the silicon wafer. Sylgard 184 PDMS (Dow Corning, Midland, Mich.) can be poured over developed photoresist to generate complementary microchannels in PDMS. The PDMS can be cured at 60° C. for 4-6 hours in an oven, following which the PDMS will be peeled off from the master. Through holes, defining the inlets and outlets, can be punched using a beveled 25-gauge needle. The bonding surfaces of the PDMS and a pre-cleaned (ultrasonicated) glass slide/wafer can be bonded following oxygen plasma treatment. Tygon Microbore tubing with an outside diameter of 0.03" and inner diameter of 0.01" connected to 30 gauge stainless steel needle can be used for world-to-chip interfacing. The completed device can be sterilized by autoclaving at 121° C. for 15 minutes and stored in sterile environment until usage. The finished devices can be tested visually for structural integrity, particularly paying attention to the post structures. The fluidic integrity of the ports and PDMS/glass slide seal can be verified at the operational flow rates.

Various devices configurations can be obtained in accordance with the invention, with internal chamber size ranging from 100 µm to 10 mm, surrounded by capillary channels of width 5 µm to 500 µm and height 5 µm to 500 µm, separated by posts 5 µm to 500 µm with gaps of 500 nm to 50 µm. In one example, the device can include a 1 mm central chamber (across) surrounded by 20 µm capillary channels (wide) with a depth of 100 µm (height of chamber and channels). The posts separating the chamber from the capillary channels can be 50 µm wide with gaps of 1 µm. FIG. 6 shows an SEM image of two channels joined by ~50 µm long slits fabricated in our laboratory with PDMS using conventional soft lithography techniques. Also, the gaps can be up to 500 nm. By comparing the yield and performance of different gap sizes in devices, tradeoffs between gap size and performance of ischemia, hypoxia, and reperfusion injury can be studied in these devices.

In one embodiment, in vitro microfluidic devices can be used to assay for analysis of MI or other conditions from ischemia and hypoxia as well as reperfusion. The device can include a plastic disposable and optically clear microfluidic chip with myocytes or other cells fed by an array of capillaries comprising of endothelial cells. Synchronized contraction of healthy myocytes can be visualized real-time. Ischemia and hypoxia of varying intensity and duration can be modeled as needed. Reperfusion injury can be created by reintroducing fluid flow after the ischemic and hypoxic conditions. Effect of both drug based therapies and recent advances in stem cell therapy can be readily tested in the device. The assay can be interfaced with 12-96 well plates (e.g., 24 well plates) for medium to high throughput assays, thereby allowing lower reagent cost, rapid turnaround times and increased biochemical knowledge to yield benefits during therapies. The device can also be used to study targeted therapy for regeneration of myocytes or other cells, such as after a reperfusion injury.

The device can include of a microfluidic chip with tissue cells (e.g., myocytes, neurons, nephrons, hepatocytes, etc.) fed by an array of capillaries comprising of vascular cells (endothelial cells). Perfusion and reperfusion of tissue cells in the internal chamber and capillary channels can be varied in intensity and duration by changes in the flow rate in the capillaries and/or directly to the internal chamber by the perfusion modulating system. The benefits of the device that can have varied flow in the channels includes: allow perfusion, occlusion and reperfusion at the rates observed in blood vessels or rates to induce a reperfusion injury; allow introduction of various insults (chemical or physical); provide real-time visualization or electrode data acquisition; and perform medium to high throughput for therapeutic screening assays. This allows the use of the device to range from pharmaceutical companies developing drugs for diseases under ischemia and hypoxia, characterize the mechanisms of ischemia and hypoxia to resolve the individual stimuli, and in drug discovery for the development of regenerative medicine, such as for overcoming a reperfusion injury. The device can be used in methods for creating ischemia induced hypoxia. The device can be used in methods for creating reperfusion injury. The device can be used in methods for creating gradients of hypoxia. The device can be idealized, or imaged with vascular and tissue spaces separated by nano to micro gaps. The device can be used in an assay for creation of ischemia induced hypoxia for cells, such as myocytes, neurons, nephrons, hepatocytes or intestinal epithelial cells. The device can be used in an assay for ischemia induced hypoxia with co-culture of cells. The device can be used in an assay to screen for chemical based ischemia. The device can be used in an assay for physical (e.g., mechanical stress) means based ischemia. The device can be used in an assay to screen for therapeutics on hypoxic cells. The device can be used to characterize key components (e.g., viability, pH/hypoxia, biomarkers) in ischemia, hypoxia, and post reperfusion injury using morphological analysis and fluorescent probes.

The device design parameters (e.g., chamber size, capillary perfusion rates and time points) can be optimized from in vivo data followed by co-culture with endothelial cells or other relevant tissue cells. Inflammation based injury following ischemia involving leukocyte interactions can also be demonstrated. The device can be integrated to a well plate format to permit higher throughput. The device can be used in methods to study stem cell therapies for regeneration of the cells (e.g., study tissue) in the internal chamber. The device can be used in methods to study drug based therapeutics for cells in the internal chamber or even in the channels. Device predictions can be compared with in vivo studies.

A well-controlled system such as the device being coupled to a perfusion modulating system can enable both drug discovery and basic understanding of cellular function before, during and after a reperfusion injury. In addition, use of an in vitro model that mimics the physiological microenvironment of the tissue being studied can reduce animal studies during the preliminary stages of the therapeutic development. Thus, the device can reproduce the critical biological characteristics of the reperfusion injury, thereby providing a valid and cost-effective tool for studying new therapeutic approaches.

The invention can provide a microfluidic device that mimics the microenvironment of a study tissue in a complex network of capillaries. Fluid flow (blood flow) in these capillaries can be readily switched on and off by the perfusion modulating system independently modulating pumps for each of the capillaries to simulate ischemia induced conditions and subsequent reperfusion. Culture of endothelial cells in capillaries beside the internal chamber with cells of the study tissue enables studies on interaction between endothelial cells and the study tissue. The device can include a plastic, disposable and optically clear microfluidic chip containing two distinct sections; an internal chamber for culture of study cells surrounded by capillaries of endothelial cells. The device is created by separating the internal chamber for culture of study tissue cells from the capillary channels lined with endothelial cells by a design utilizing large posts. The posts create islands which are separated by submicron-micron gaps to ensure diffusion based fluidic connection between the capillary channels and the internal chamber leading to a microenvironment observed in vivo with myocytes being surrounded by capillaries. The perfusion modulating system can be operably coupled with the individual channels and internal chamber to independently modulate perfusion to stop flow and reintroduce flow for reperfusion analysis.

The device can include a reproduction of complex microvascular networks onto plastic (e.g., PDMS) substrates. These networks, originally rendered from in vivo images of tissues, allow quantitative study of drug particle adhesion to and transfection of vascular endothelial cells in circumstances closely mimicking in vivo conditions. This methodology was used to create devices from a microvascular network of hamster cremaster muscle in vivo ranging from 15-100 μm. FIG. 2A shows an example of the complete microvascular network on the microfluidic chip with a magnified view of microchannels in FIG. 2B.

In one embodiment, a cell culture system can include: the device of one of the embodiments; and a perfusion modulating device coupled to the port of the internal chamber and/or to the port of the at least one fluidic channel.

In one embodiment, a method of inducing ischemia and reperfusion can include: providing the device of one of the embodiments having a first cell culture in the internal chamber and a second cell culture in the at least one fluid channel; modulating perfusion in the internal chamber with the perfusion modulating device to induce ischemia and then reperfusion injury; and assaying for ischemia and/or reperfusion injury in the first cell culture. In one aspect, the method can include modulating perfusion in the at least one fluid channel for ischemia and then for reperfusion injury. In one aspect, the method can include varying intensity and duration of fluid flow in the at least one fluid channel so as to vary perfusion in the internal chamber to reduce perfusion or stop perfusion, and then reintroduce perfusion to cause reperfusion injury. In one aspect, the method can include introducing a chemical and/or physical insult to the first cell culture in the internal chamber. In one aspect, the method can include inducing gradients of hypoxia in the internal chamber. In one aspect, the method can include inducing hypoxia in myocytes, neurons, nephrons, or hepatocytes or cells of any other tissue in the internal chamber and then causing reperfusion injury to these cells. In one embodiment, the method can include screening therapeutics on reperfusion injured cells in the first cell culture in the internal chamber. In one embodiment, the method can include characterizing viability, pH, hypoxia, or biomarkers in cells in the first cell culture in the internal chamber after reperfusion injury. In one embodiment, the method can include regenerating cells the internal chamber after reperfusion injury. In one embodiment, the method can include visualizing cells in the first cell culture in the internal chamber before, during or after reperfusion injury. In one embodiment, the method can include simulating a reperfusion injury in the first cell culture of myocytes in the internal chamber. In one embodiment, the method can include inhibiting fluid flow in the internal chamber sufficient to induce low to moderate ischemia and then reintroducing the fluid flow for causing a reperfusion injury. In one embodiment, the method can include inhibiting fluid flow in the internal chamber and at least one fluid channel sufficient to induced moderate to severe ischemia and then reintroducing fluid flow for causing a reperfusion injury.

In some embodiments, the perfusion modulating system can include a controller that can control the individual pumps and/or valves or other fluid flow devices, which allows for selectively controlling flow rate of media having oxygen, media without oxygen, or oxygen or air through each individual capillary channel and each internal chamber. The controller can be configured as a computer that can provide operational data to the pumps to control the pumping action, and thereby control the flow, occlusion of flow, and reperfusion flow rates. The perfusion modulating system may include one or more flow meters that monitors the flow and provides flow data to the controller, and thereby the controller can change operational data to change the operation of the pumps for maintaining flow, increasing flow, decreasing flow, and stopping flow in any order or in any sequence combination.

In some embodiments, the systems and methods described herein can be used for modeling an ischemic reperfusion injury (IRI). The IRI can occur when blood supply, perfusion, and oxygenation is restored to an organ or area following an initial poor blood supply (hypoxia) after a critical time period. These stages can be performed with the perfusion modeling system modulating fluid flow in the capillary channels and internal chamber of the cell culture device. The perfusion modulating system can cause an IRI by causing reperfusion that leads to damage to cells of different organs in the internal chamber, or to the cells in the capillary channels. The calls in the internal chamber can be from organs including brain, cardiac, kidney, liver and intestine, among others. The IRI results from several complex mechanisms that involve the production of reactive oxygen species (ROS), alterations in intracellular calcium handling, microvascular and endothelial cell dysfunction, altered cellular metabolism, and activation of neutrophils, platelets and complement. Any of these mechanisms can be assayed for with the present cell culture device and perfusion modulating system. The ROS are considered key molecules in reperfusion injury due to their potent oxidizing and reducing effects that directly damage cellular membranes. The ROS also activate endothelial cells elevating adhesion molecules that play a major role in the interactions between the neutrophil and the endothelium. Major ROS involved include superoxide anion, hydrogen peroxide, hydroxyl radical, nitric oxide and peroxynitrite. Accordingly, these substances can be monitored for amounts or changes in amounts post IRI. Other contributors for IRI include eicosanoids comprising prostaglandins, thromboxanes and leukotrienes, any of which can be monitored for amounts or changes in amounts post IRI. Additional molecules that lead to the injury are nitric oxide, endothelin, cytokines, complement activation factors and proteases, any of which can be monitored for amounts or changes in amounts post IRI. The amounts of these substances may be monitored as per their concentration in the cell culture medium.

In some embodiments, the cell culture device can be used with the perfusion modulating system in methods to model, monitor and study therapeutics for ischemia reperfusion injury. The ischemia conditions can be created by modulating the flow through the cell culture device, or modulating clot formation in the case of blood flow. Reperfusion can be modulated by varying the flow volumes using valves and pumps to create pressure differences or in the case of blood by dissolving the blood clot using chemical or mechanical forces. The proposed system can monitor injury using optical or electrical methods, such as with electrodes inserted through the ports into the internal chamber and/or capillary channels. Electrodes present in the cell culture device allows for real-time non-invasive monitoring. Use of both 2D and 3D electrodes demonstrate applicability for thin (<100 μm) and thick slices >100 μm to centimeter size of tissue mimicking models.

In some embodiments, the methods of creating a reperfusion injury can be performed in accordance with any method described herein with the step of reperfusing fluid flow through the cell culture device, such as through the internal chamber and/or capillary fluid channels. For example, the steps in creating the reperfusion injury can include: Step 1) culture cells in 2D or 3D matrix in a cell culture device of any embodiment; Step 2) subject cells to ischemia and hypoxia for a desired duration of time by creating an oxygen reduced or deprived environment or modulation of nutrients via fluid flow (e.g., by perfusion modulating system). During Step 2, it can be optional to measure the activity or other features (e.g., described herein) of the cells using optical assays or electrical signals; Step 3) initiate reperfusion of oxygen and/or media flow based nutrients at varying concentrations (e.g., with the perfusion modulating system); and Step 4) measure the cellular responses using optical or electrical signals to determine levels of injury.

In some embodiments, the cell cultures in the cell culture device can be monitored before, during, and after the protocol, such as before, during, or after each step. The cell cultures can be tracked to determine any changes that occur as a result of any of the steps. This allows for real-time monitoring of the conditions of the cells and changes thereto as a result of the reperfusion. For example, the monitoring can be performed to allow for characterizing viability, pH, hypoxia, or biomarkers in cells in the first cell culture in the internal chamber before, during and/or after reperfusion injury In some embodiments, the methods can optionally include Step 5) repeat process and additionally modulate the system, such as by injecting therapeutics, biomolecules, chemicals, or the like into the cell culture device (e.g., internal chamber and/or capillary channels with the perfusion modulating system) to reduce the level of injury and determine mechanism of actions.

Figure 8A:
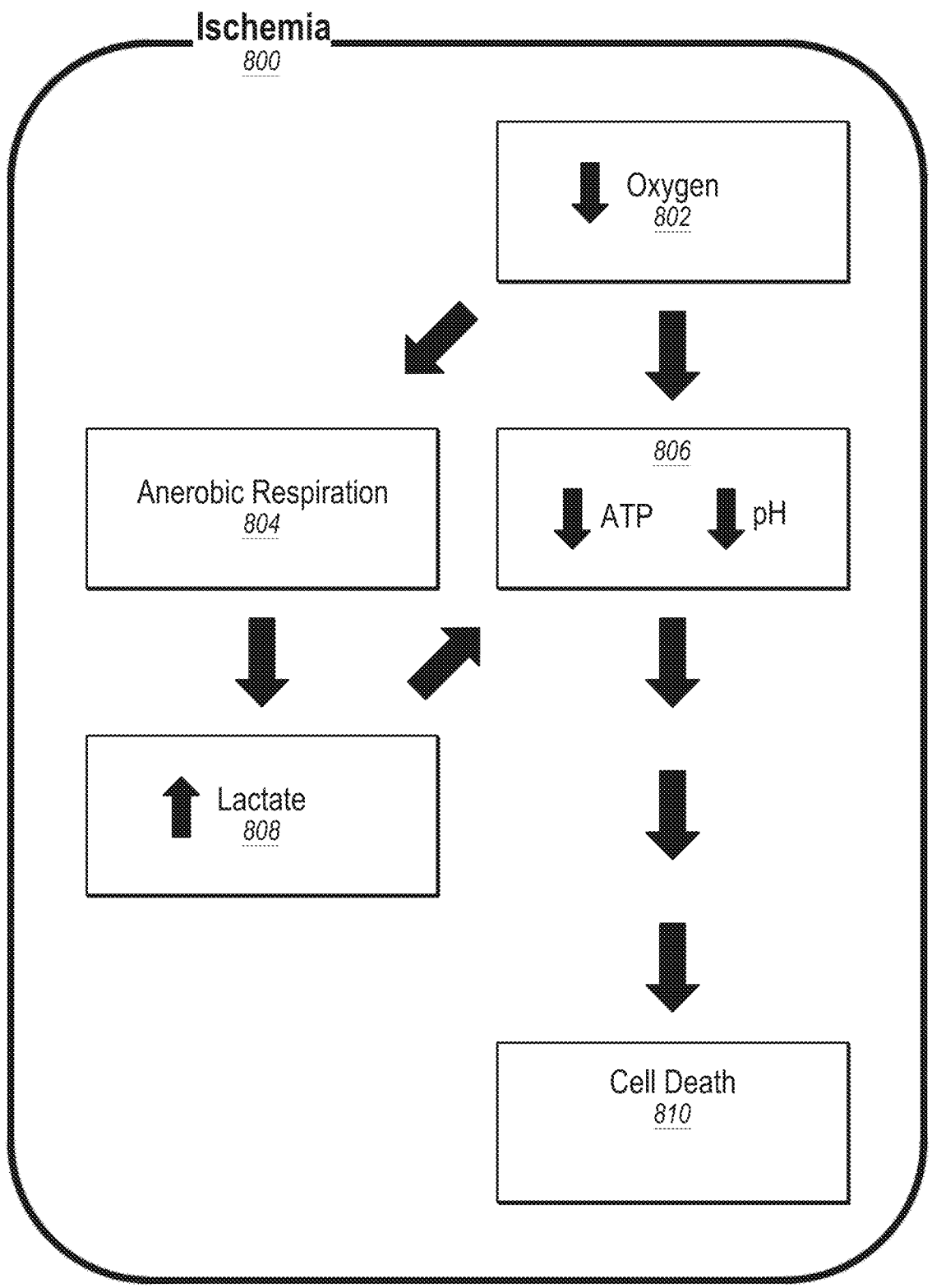
FIG. 8A illustrates an embodiment of a method of inducing ischemia.

FIG. 8A shows a method for inducing ischemia 800, which includes: reducing oxygen (block 802); causing anaerobic respiration from lack of oxygen (block 804); reducing ATP and pH (block 806); causing an increase in lactate (block 808); and causing cell death (block 810) from the increased lactate, reduced ATP, and reduced pH, among other reasons.

Figure 8B:
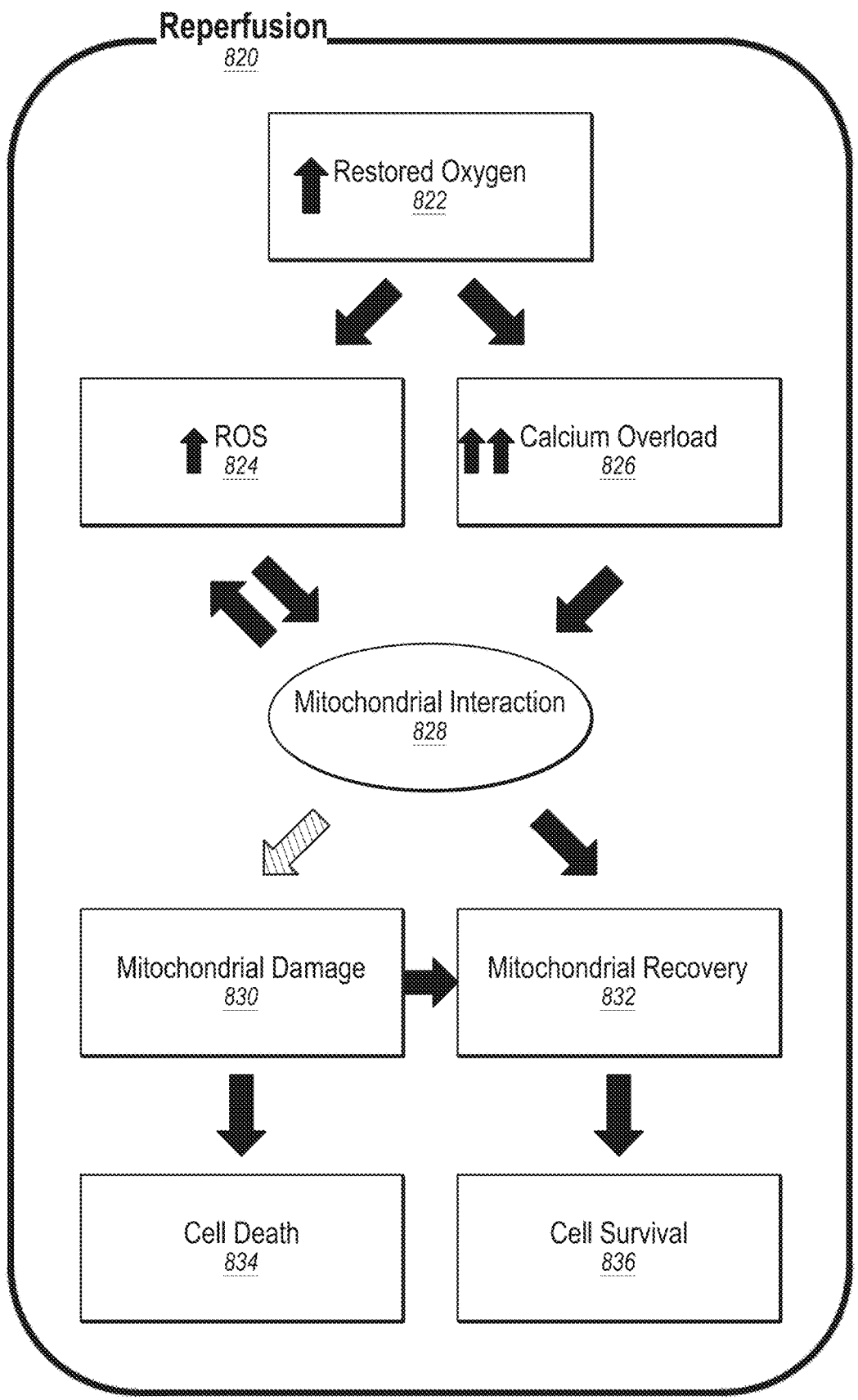
FIG. 8B illustrates an embodiment of a method of causing reperfusion injury with cell death and/or cell survival.

FIG. 8B shows a method for causing a reperfusion injury 820, which includes: restoring oxygen to the cell culture (block 822); causing reactive oxygen species to be formed or released (block 824); causing calcium overload (block 826), which may be significant calcium overload as shown by two up arrows; and causing mitochondrial interaction with the reactive oxygen species and/or calcium (block 828). After causing injury from reperfusion, such as by the mitochondrial interaction, two pathways may be monitored in the cell. The mitochondria may be damaged (block 830), which can lead to cell death (block 834). The damaged mitochondria may recover (block 832) upon treatment or if not sufficiently damaged to cause cell death. The second pathway can include mitochondrial recover (block 832) and cell survival (block 836). The methods can monitor the cells through any of the steps shown in FIGS. 8A-8B. The cell death and cell survival can be assessed to determine the health of the cells. In some instance, the mitochondrial recovery can be due to some therapeutic regime or treatment.

Figure 7:
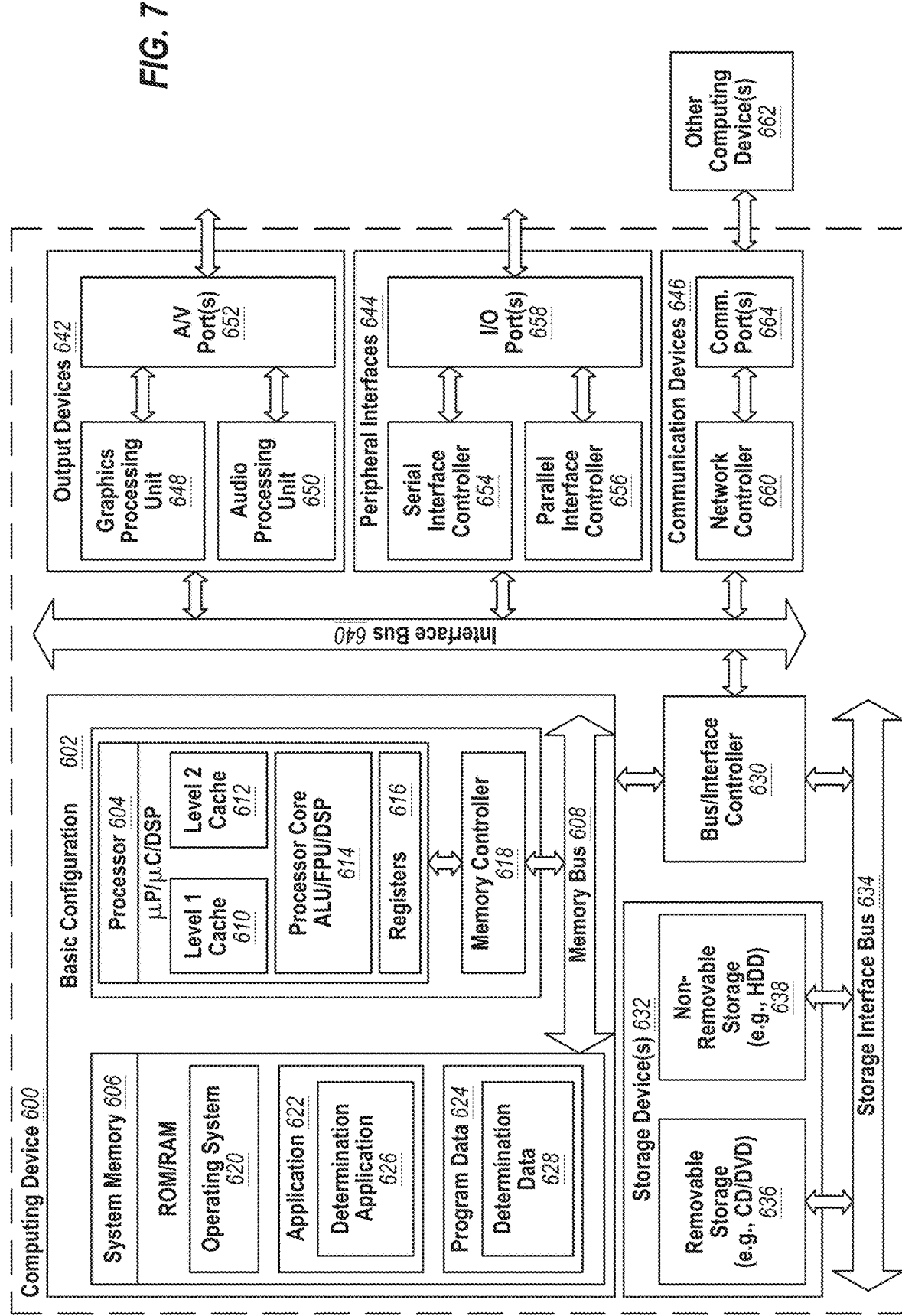
FIG. 7 illustrates an embodiment of a computing system, which can be used as a system controller and data analyzer.
Figure 9A:
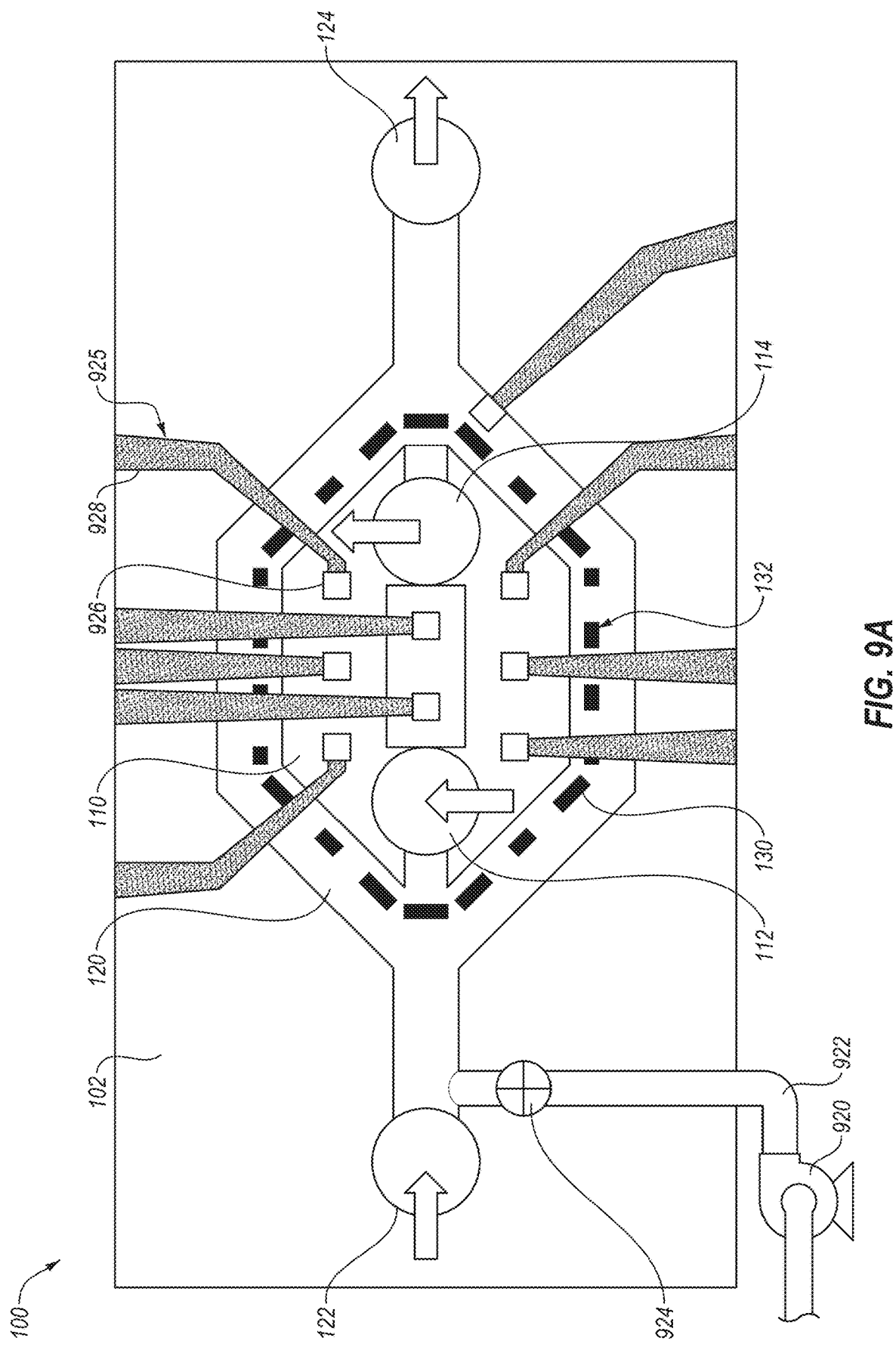
FIG. 9A illustrates an embodiment of a cell culture device for use in ischemia, hypoxia, and reperfusion assays with fluid flow controlled with a perfusion modulating system and embedded electrodes for biological analysis.

FIG. 9A shows a modified cell culture device 100 in accordance with FIG. 1A, which has been modified with a pump 920 connected through a fluid conduit 922 and valve 924 to the inlet 122. However, any number of pumps 920, fluid conduits 922, and valves 924 can be included and placed at any location relative to the channel 140 or internal chamber 110. The pump 920 and valve 924 can be used to regulate fluid pressure in the system, which can be controlled with the controller (FIG. 7). The pump 920 can be coupled with a fluid supply, such as a reservoir or recycling system that recycles the media, and which can operate as part of the perfusion modulating system 900. Additionally, electrodes 925 can be included at various locations to monitor the cell cultures, where the electrodes 925 can include conductive pad 926 and electrode traces 928. The electrode traces 928 may be coated with a non-conductive material, which may be biocompatible. For example, the electrodes 925 can be in the internal chamber 110 and/or within any capillary channel 120 or barrier channel as described herein. The electrodes can be coupled with a controller or other computing system to obtain the data for analysis of the cell cultures, such as in relation to the creation of a reperfusion injury.

Figure 9B:
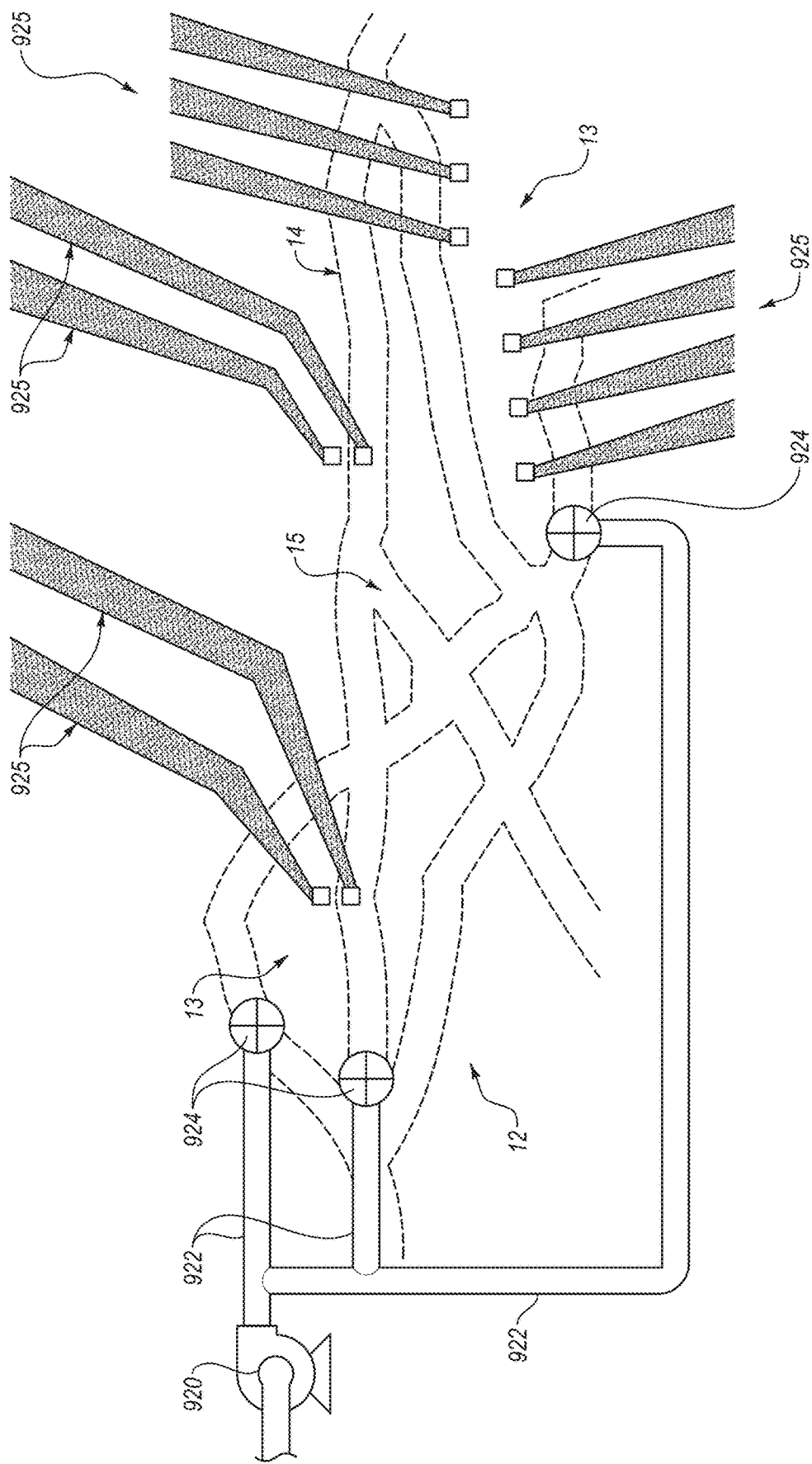
FIG. 9B illustrates an embodiment of a cell culture device having an internal chamber and fluid channels that are modeled from physiological features with fluid flow controlled with a perfusion modulating system and embedded electrodes for biological analysis.

FIG. 9B shows a modified cell culture device with a synthetic microvascular network (SMN) 12 having internal chambers 13 surrounded by channels 14 in accordance with FIG. 2A, which has been modified with a pump 920 connected through fluid conduits 922 and valves 924 to the channels 14. However, any number of pumps 920, fluid conduits 922, and valves 924 can be included and placed at any location relative to the channels 14 or internal chamber 13. The pump 920 and valve 924 can be used to regulate fluid pressure in the system, which can be controlled with the controller (FIG. 7). The pump 920 can be coupled with a fluid supply, such as a reservoir or recycling system that recycles the media, and which can operate as part of the perfusion modulating system 900. Additionally, electrodes 925 can be included at various locations relative to the internal chambers 13 and channels 14 to monitor the cell cultures, where the electrodes 925 can include conductive pad 926 and electrode lead 928. The electrode leads 928 may be coated with a non-conductive material, which may be biocompatible (e.g., silicone coating). For example, the electrodes can be in the internal chamber 13 and/or within any channel 14 as described herein. The electrodes 925 can be coupled with a controller or other computing system to obtain the data for analysis of the cell cultures, such as in relation to the creation of a reperfusion injury.

Figure 9C:
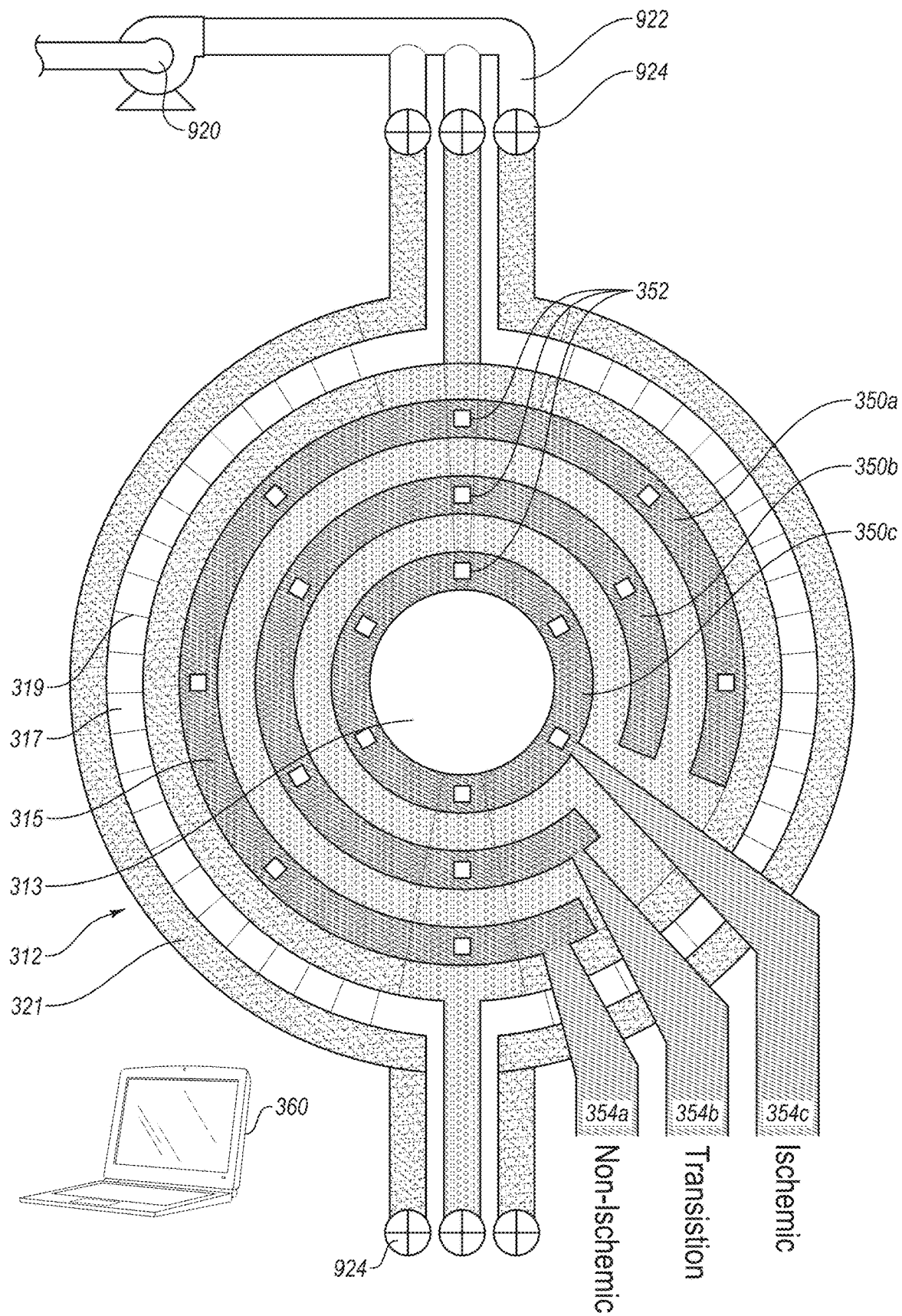
FIG. 9C illustrates an embodiment of a circular cell culture device having an internal chamber and fluid channels that are idealized and with fluid flow controlled with a perfusion modulating system and embedded electrodes for biological analysis.

FIG. 9C shows a modified cell culture device configured as a round IMN 312 in a microfluidic chip. The IMN 312 includes a round tissue space 313 surrounded by a barrier space 315, which is surrounded by a wall 317 having gaps 319, and where an outer capillary channel 321 is on the outside. As shown, the barrier space 315 can include posts or pillars for cell culturing tissue, and may be an arbitrary region adjacent to the wall 317. Here, the round tissue space 313 is shown to include an inlet and an outlet on opposite sides thereof, which inlet and outlet can be coupled with a pump of the perfusion modulating system. Also, the outer capillary channels 321 each include an inlet and an outlet on opposite sides thereof, which inlet and outlet for each channel can be coupled to an individual pump of the perfusion modulating system. Thus, the prefusion modulating system can include a pump for each channel or each chamber.

The cell culture device can include annular electrodes 350a,b,c within the tissue space 313 and the boundary space 315. As shown, inner annular electrode 350c is completely circular; middle annular electrode 350b and outer annular electrode 350a are "C" shaped annular electrodes with a gap between the ends. The gaps are illustrated to be staggered from the middle annular electrode 350b to outer annular electrode 350a. In some aspects, each annular electrode 350a,b,c is a conductor and the entirety functions as a conductive pad. In some aspects, each annular electrode 350a,b,c includes one or more conductive pads 352. In some aspects, some of the conductive pads 352 on one annular electrode 350b may be aligned with conductive pads 352 on the adjacent electrode 350a,c. In some aspects, some of the conductive pads 352 can be staggered, random, or in any pattern relative to the other conductive pads on any of the annular electrodes. As shown, each annular electrode 350a,b,c includes a conductive pad 352 radially aligned with a conductive pad 352 of the other annular electrodes. The conductive pads 352 can be used to measure electrical data of the cells in the cell culture. While FIG. 9C is a top view, the annular electrodes 350a,b,c can be 2D or have a thin thickness, such as an electrical trace of conductive film. Each annular electrode 350a,b,c is electrically coupled to an electrode lead 354a,b,c. The annular electrodes 350a,b,c (except for conductive pads) and/or electrode leads 354a,b,c may be coated with a non-conductive material, which may be biocompatible (e.g., silicone). The electrode leads 354a,b,c can be coupled with a controller or other computing system to obtain the data for analysis of the cell cultures, such as in relation to the creation of a reperfusion injury.

In some embodiments, the annular electrodes 350a,b,c are 3D with a significant thickness so that they form walls. Here, the annular electrodes 350a,b,c have a height extending from a base surface so as to form concentric walls with respect to each other with the middle annular electrode 350b and outer annular electrode 350a having gaps so that fluid (e.g., media, oxygen, etc.) can pass between the regions around the annular electrodes 350a,b,c. The annular electrodes 350a,b,c can extend to a top surface or lid of the device 312.

Figure 1B:
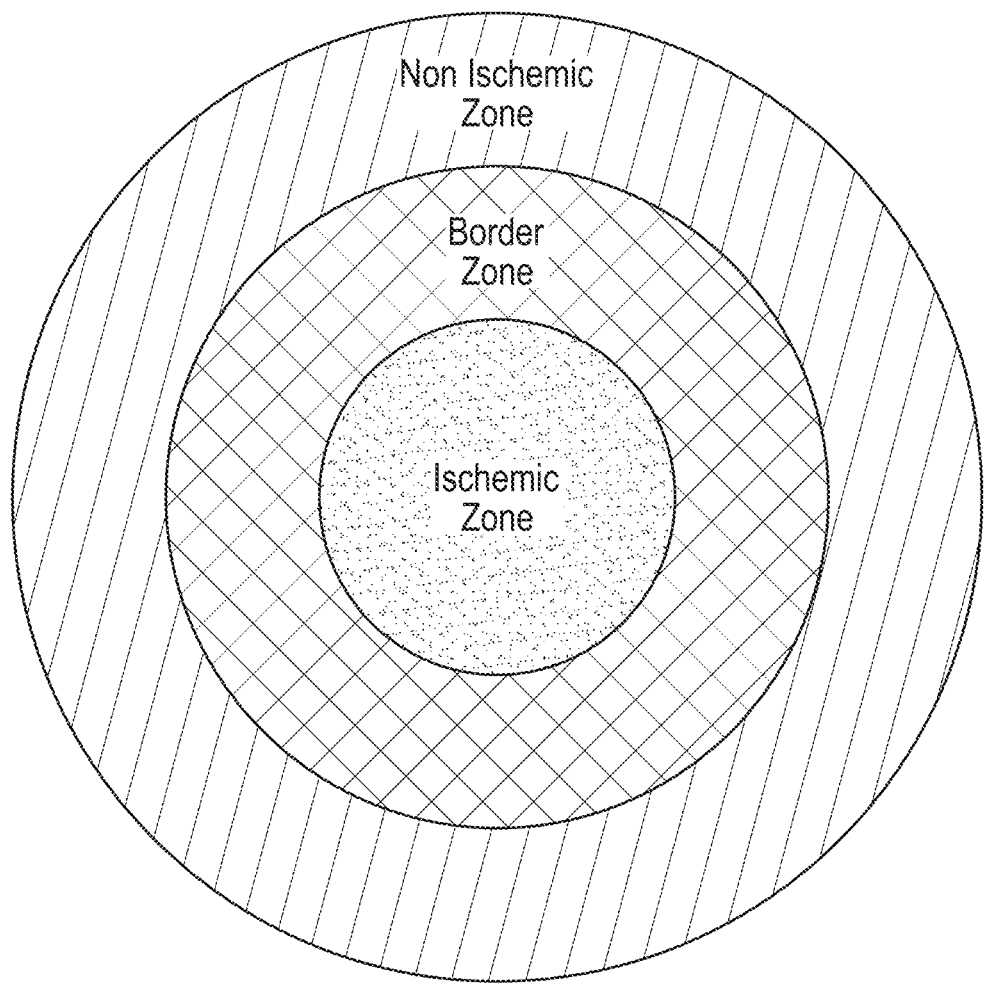
FIG. 1B illustrates a representation of ischemia zones in the internal chamber of the cell culture device.

In some embodiments, the annular electrodes 350a,b,c can be configured such that the inner electrode 350c is for a region that is ischemic. The middle electrode 350b is for a transition region. The outer electrode 350a is for a non-ischemic region. As such, the electrodes 350a,b,c correspond to the three regions shown in FIG. 1B. As such, the cell activity can be monitored at each location by the different annular electrodes 350a,b,c. This can test cells that are in the three different regions. Accordingly, the different levels of ischemic condition can be analyzed for response to the reperfusion injury that is created by the perfusion modulating system.

Additionally, the perfusion modulating system can include a pump 920 coupled to the valves 924 via the channels 922. At the other end, the valves 924 can be coupled to a recycle system, waste, assay system, fluid analysis system, cell analysis system, or the like, such as being fluidly coupled to the perfusion modulating system. The pump(s) 920 and valves 924 can be individually operated to be on or off in any pattern, which can be controlled by a controller 360 (e.g., computer). The controller 360 can be interfaced by an operator or be under the control of automated software to run a routine that includes selective fluid flow, selective reduction or stoppage of fluid flow to induce hypoxia, and then reperfusion fluid flow to cause a reperfusion injury. The controller 360 or other computer may receive the electrode data from the annular electrodes 350a,b,c so that different cellular conditions can be monitored for different locations relative to an ischemic condition (e.g., 3 regions).

Figure 10:
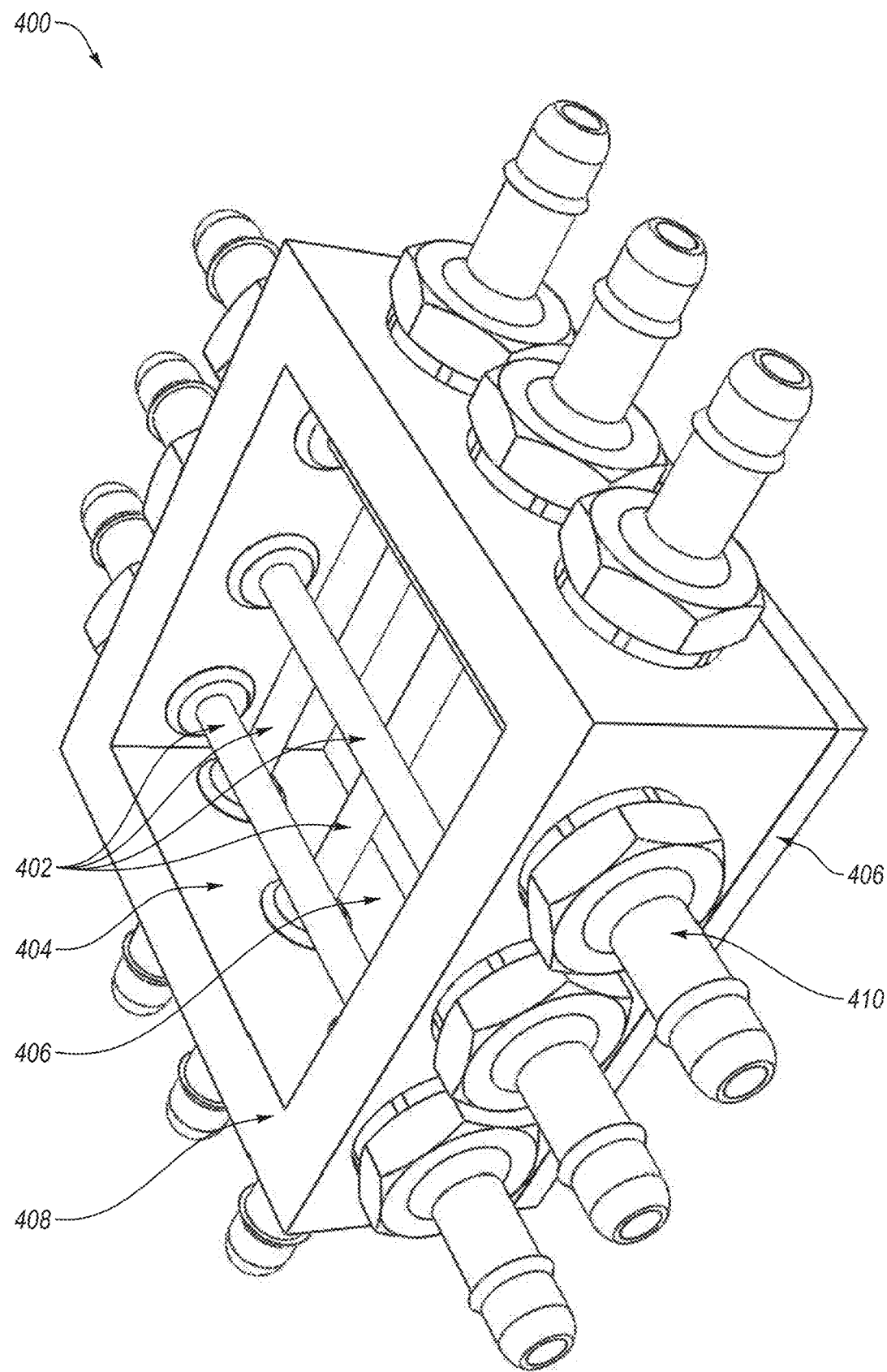
FIG. 10 illustrates an embodiment of a tissue construct device with an array of channels for fluid flow which can be regulated for reperfusion flow in a thick tissue construct made of native and synthetic hydrogels and/or native and synthetic extracellular matrix.

FIG. 10 illustrates a cell culture device 400 with an array of channels 402 passing through an internal chamber 404 for fluid flow, which can be regulated for reperfusion flow in a thick tissue construct made of hydrogels and/or extracellular matrix holding cells. The fluid flow can be controlled by the perfusion modulating system to be through a single channel, through a combination of multiple channels, through all channels of the array at any time for any duration. This allows each channel to be individually controlled to be on or off, and to control the flow rate therethrough. For example, one or more pumps and/or valves can be modulated to modulate the flow for each channel independently of the other channels The thick tissue construct can be formed in the internal chamber 404 that is defined by the base 406 and sidewalls 408, and a top (not shown, e.g., lid, cover, etc.). The sidewalls 408 include fluid connectors 410 that are adapted to be coupled with tubing, and the tubing connects to the valves and pump(s) of the perfusion modulating system. The channels 402 are porous (e.g., dimensions of gaps, holes, apertures, etc.) to allow for fluid flow (e.g., media and/or oxygen) from the channels 410 into the thick tissue construct growing therein having cells. As shown, base 406 is removable from the sidewalls 408 and operates as a removable covering, which may also be used as a top as a lid. One or more of the base 406 can be removed and two or more of the cell culture devices 400 can be stacked to change the dimensions of the cell culture space by combining multiple internal chambers 404 into a larger space. Accordingly, the cell culture device 400 is a modular configuration that is stackable to vary dimensions of the tissue construct being tested. Each modular component includes the array of channels 402.

Figure 11:
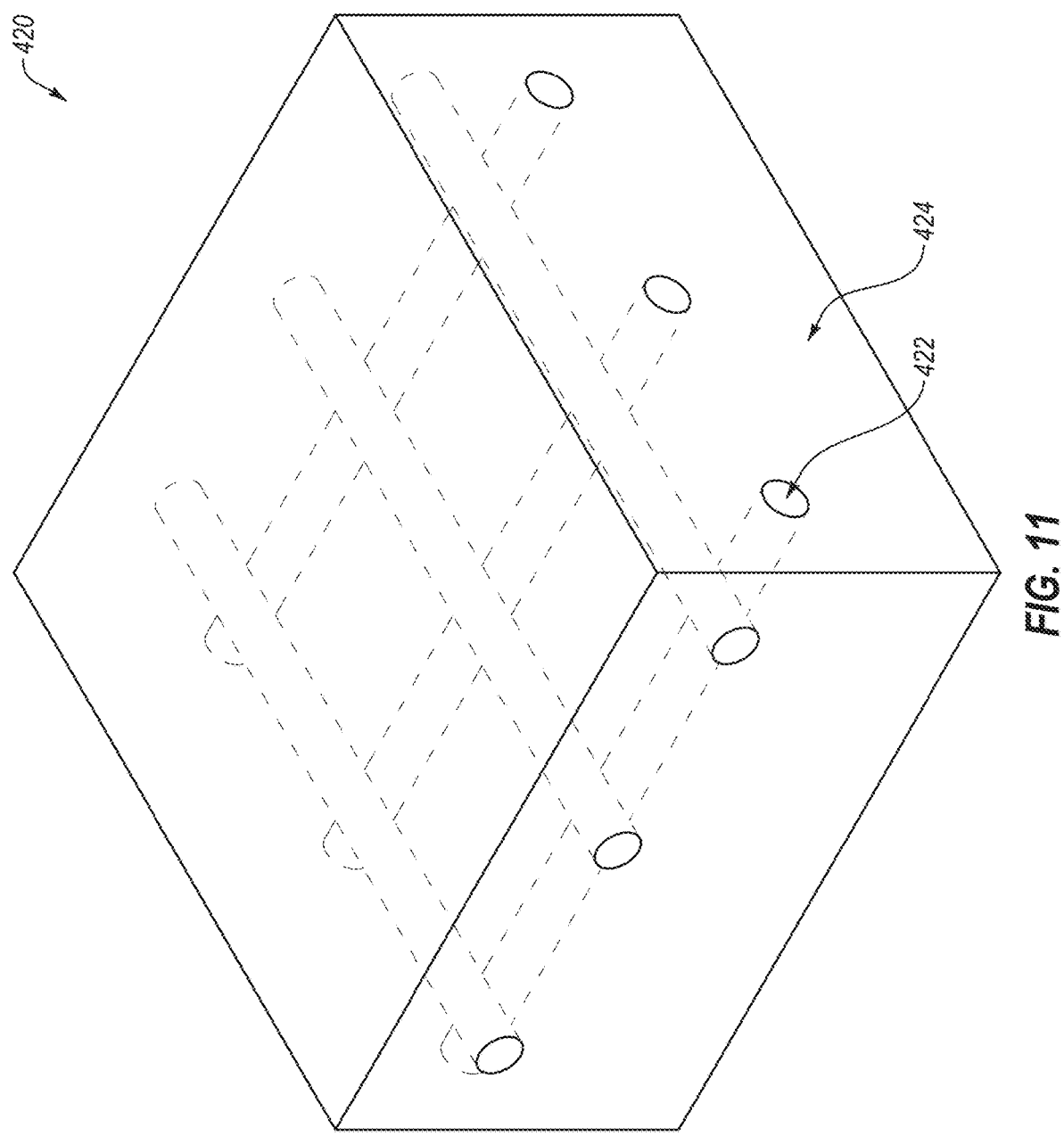
FIG. 11 illustrates another embodiment of a tissue construct device with an array of channels for fluid flow which can be regulated for reperfusion flow in a thick tissue construct made of native and synthetic hydrogels and/or extracellular matrix.

FIG. 11 shows another embodiment of a cell culture device 420 that has an array of channels 422 formed into a body 424. In some aspects, the body 424 can be a tissue construct with the array of channels 422 formed therein. In some aspects, the body 424 can also include an internal chamber formed therein around the channels 422. The channels 420 are porous and have apertures or gaps as shown by the dashed lines to allow for controlling perfusion and reperfusion into a cell culture or tissue construct. Each of the channels 420 can be connected via fittings, tubing and the like to valves and pumps for control of the flow of fluid, and thereby control the perfusion. In some embodiments, the body 424 is a tissue construct formed from hydrogels and/or extracellular matrix having the channels 422 formed therein, wherein the tissue construct includes cells of the tissue.

In some embodiments, the different channels can be connected to different fluid sources. For example, some may be connected to media devoid of oxygen, some to media having oxygen, and some to oxygen or air. The different flows can be controlled to create different environments in the cell cultures or tissue constructs to provide different levels of hypoxia and different results from the reperfusion injury.

Figure 12A:
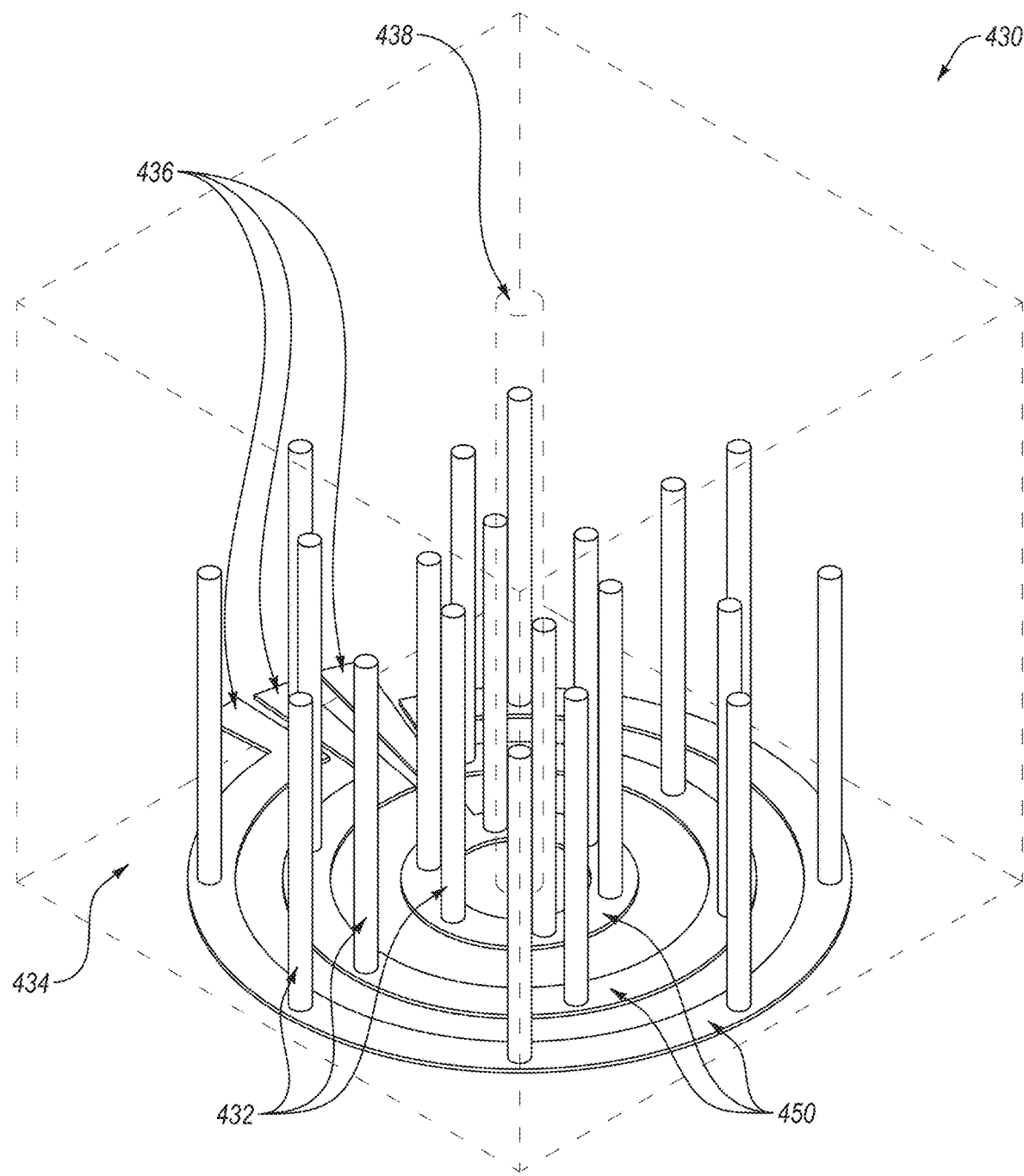
FIGS. 12A-12C include different view of an embodiment of a device having vertically aligned electrodes (e.g., 3D) spanning the entire thickness of the tissue construct fabricated using hydrogels and/or extracellular matrix to support cellular growth.
Figure 12C:
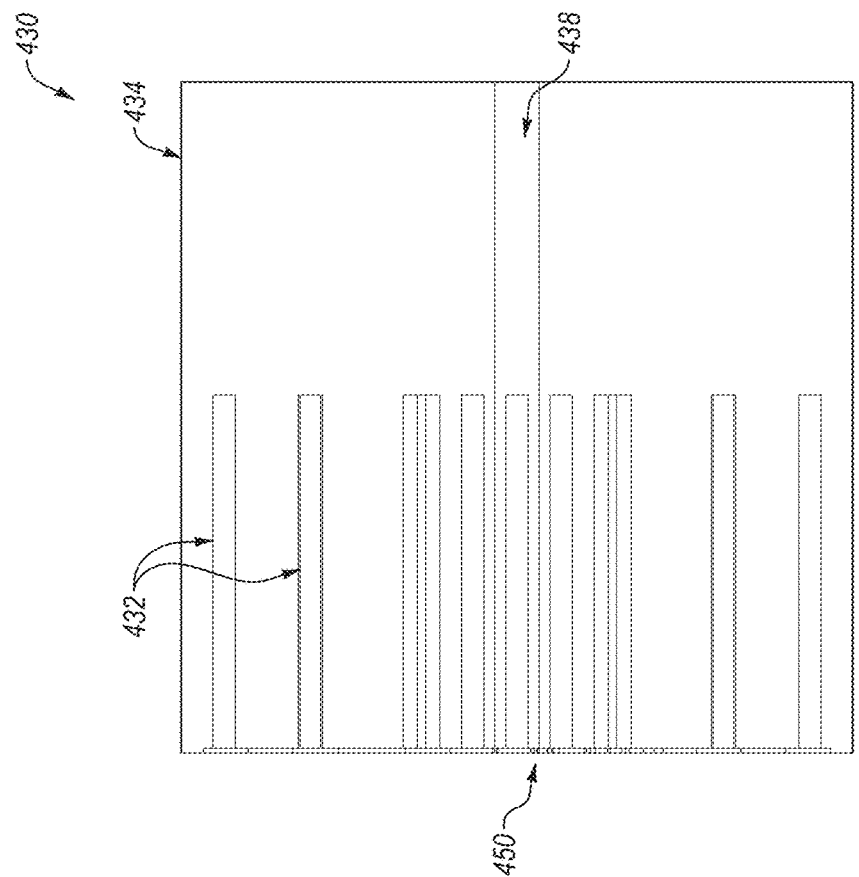
Figure 12B:
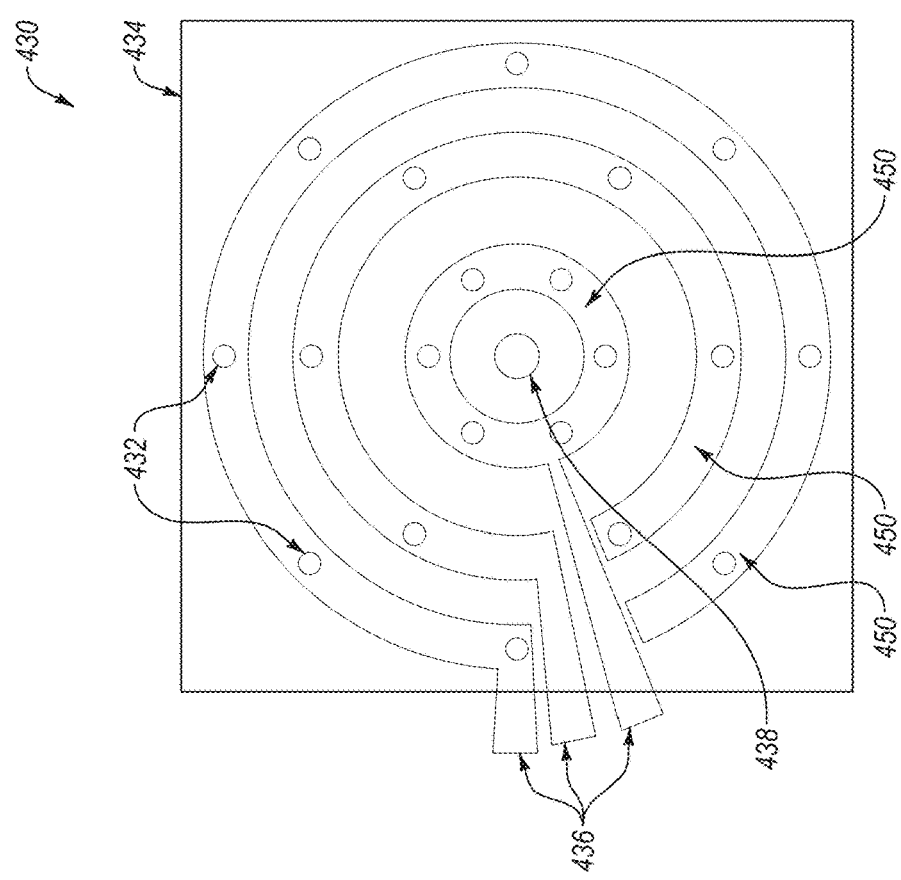

FIGS. 12A-12C illustrate a cell culture device 430 that has vertically aligned electrodes 432 (3D) spanning the entire thickness of a body 434, where each vertical electrode 432 is connected to an annular electrode 450. Each annular electrode 450 can include an electrical end 436 that is configured to be electrically connected to an electrode data acquisition unit (e.g., computer). Each independent vertical electrode 432 can have any height/length as desired, and can protrude from the annular electrode 450 at any distance with any dimensions. The length and width dimensions can be modulated as desired. The varying length of electrodes 432 can result in combination of electrodes 432 with the same length, different lengths, and any combination of lengths. The lengths of the electrodes 432 can be adapted to span any depth of the tissue construct, such as all the way through or any portion thereof. As shown, the center of the body 434 includes a fluid flow channel 438 from the top to the bottom, and with openings that can be coupled to tubing of a perfusion modulating system. Any number of flow channels 438 and in any orientation or position or any angle can be included. The three different annular electrodes 450 can be used for different levels of ischemia, such as ischemic further away from the flow channel 438 a non-ischemic region next to the flow channel 438 and a transition region between the ischemic region and non-ischemic region, where each region has its own annular electrode 450 for assays the cells before, during and after a reperfusion injury. In some embodiments, the body 434 is a tissue construct fabricated using hydrogels and/or extracellular matrix formed around the electrodes 432 and flow channel 438. In some embodiments, the body 434 is a device that has an internal chamber therein formed around the electrodes to hold a cell culture.

In some embodiments, the electrode configuration of FIG. 12A can be used in the cell culture device of FIG. 9C, or others.

In some embodiments, the structures of the electrode systems described herein, such as in FIGS. 9A-9C and 12A-12C can be designed and manufactured. The electrode systems can be designed on a computer to include shapes that conform with shapes of cell culture devices. For example, the electrode system can be designed to be shaped for an internal chamber of synthetic microvascular network (SMN) or idealized microvascular network (IMN). The electrodes can be designed on a computing system by utilizing CADs of the tissue culture chambers and channels of a cell culture device, and then determining the number of electrodes and placement of the electrodes in the cell culture device, which can include determining the number, shape, size, placement or other design parameter of electrode pads, vertical electrodes, annular electrodes with or without electrode pads, or any other parameter. The design can then be provided to a manufacturing system for production of the electrode system.

In some embodiments, the microelectrode array (MEA) can be produced with standard techniques. In some embodiments, the MEA can be manufactured with traditional stereolithographic methods. A typical manufacturing process for a 2D or thin MEA can be as follows: 1) patterning of a negative photoresist atop indium-tin oxide coated class; 2) sputter coating with gold or other biocompatible, conductive material; 3) stripping of photoresist; 4) patterning of positive photoresist; 5) etching of indium-tin oxide layer and positive photoresist to create traces; 6) positive photopatterning of an insulating layer, such as SU-8. In some embodiments, the process can be configured to build 3D MEA structures, which can include multiple negative and positive patterning of the initial photoresist followed by sputter coating until building a suitable thickness or height of the 3D electrodes (e.g., forming walls). Other methods of producing 3D MEAs include micro-machining of silicon followed by etching to expose electrode contacts, or patterning of electrodes along silicon shanks.

Figure 13:
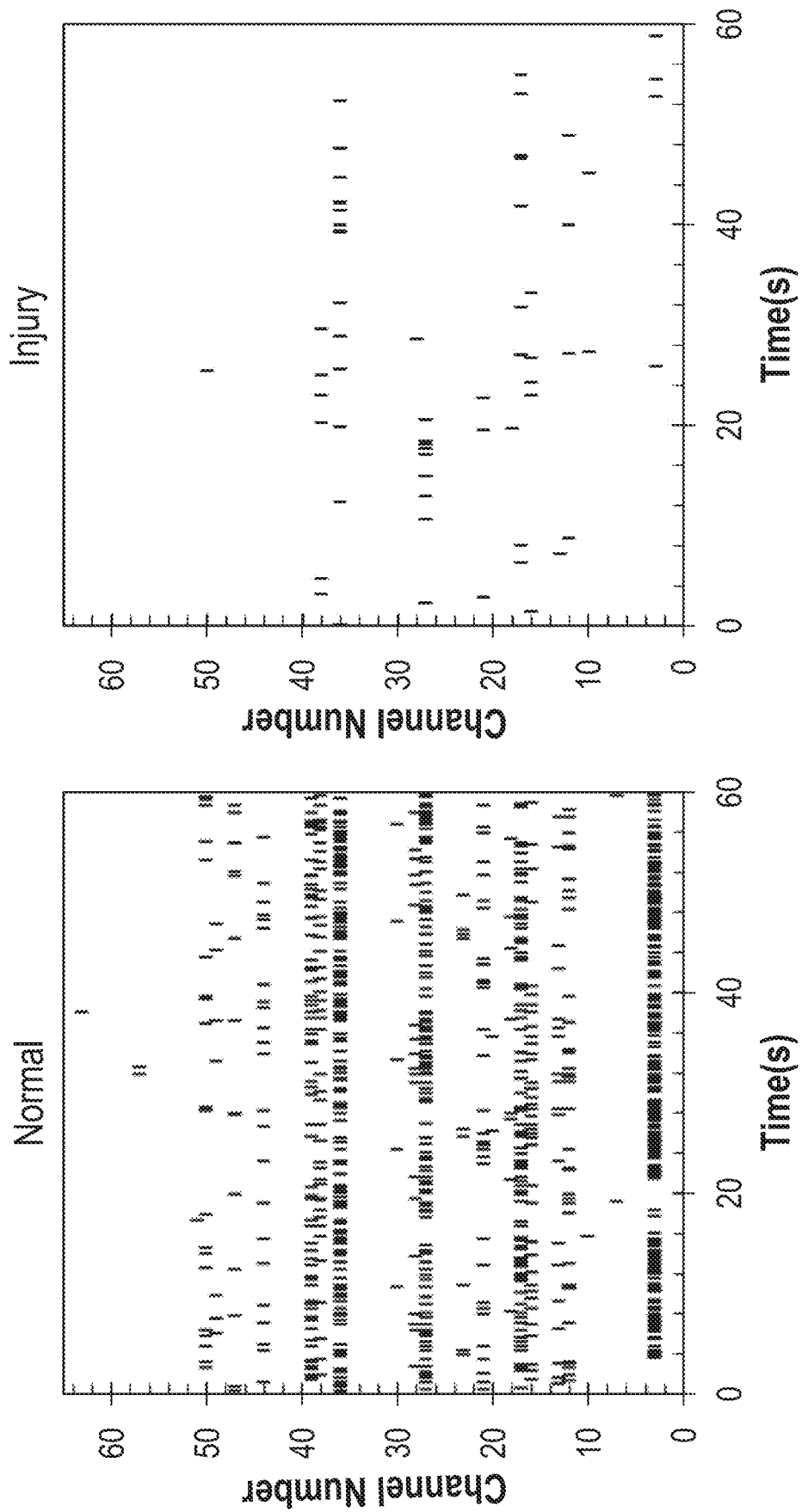
FIG. 13 shows data for the electrodes that receive electrical signals from normal cells prior to a reperfusion injury (Normal) and receive significantly less electrical signals from cells after a reperfusion injury (Injury), which show sample examples of cellular activity measured using electrodes.

FIG. 13 includes two graphs that show the number of electrodes that are receiving data from live cells (Normal) and the lower number of electrodes that are receiving data from live cells after a hypoxia/reperfusion injury (Injury). As shown, there is a significant reduction in functionally active and/or viable cells and increase of apoptotic cells after the reperfusion injury, which is shown by the reduction of marks of the channel number decreasing after the injury.

In one embodiment, the present methods can include aspects that are controlled with a computing system. For example, the computing system can be configured as a controller for the perfusion modulating system, and can control the pumps thereof, such as during perfusion, stopping flow, and reperfusion. As such, the computing system can include a memory device that has the computer-executable instructions for performing the steps of the methods described herein. The computer-executable instructions can be part of a computer program product that includes one or more algorithms for performing any of the method steps of any of the claims.

In one embodiment, any of the operations, processes, or methods, described herein can be performed or cause to be performed in response to execution of computer-readable instructions stored on a computer-readable medium and executable by one or more processors. The computer-readable instructions can be executed by a processor of a wide range of computing systems from desktop computing systems, portable computing systems, tablet computing systems, hand-held computing systems, as well as network elements, and/or any other computing device. The computer readable medium is not transitory. The computer readable medium is a physical medium having the computer-readable instructions stored therein so as to be physically readable from the physical medium by the computer/processor. The computing system can be operably coupled with the pumps of the perfusion modulating system. The computing system may also control: temperature by controlling heating and/or cooling units; carbon dioxide by controlling carbon dioxide flow into the cell culture device; oxygen by controlling oxygen flow into the cell culture device; or other parameters.

There are various vehicles by which processes and/or systems and/or other technologies described herein can be effected (e.g., hardware, software, and/or firmware), and that the preferred vehicle may vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The various operations described herein can be implemented, individually and/or collectively, by a wide range of hardware, software, firmware, or virtually any combination thereof. In one embodiment, several portions of the subject matter described herein may be implemented via application specific integrated circuits (ASICs), field programmable gate arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware are possible in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a physical signal bearing medium include, but are not limited to, the following: a recordable type medium such as a floppy disk, a hard disk drive (HDD), a compact disc (CD), a digital versatile disc (DVD), a digital tape, a computer memory, or any other physical medium that is not transitory or a transmission. Examples of physical media having computer-readable instructions omit transitory or transmission type media such as a digital and/or an analog communication medium (e.g., a fiber optic cable, a waveguide, a wired communication link, a wireless communication link, etc.).

It is common to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. A typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems, including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. Such depicted architectures are merely exemplary, and that in fact, many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include, but are not limited to: physically mateable and/or physically interacting components and/or wirelessly interactable and/or wirelessly interacting components and/or logically interacting and/or logically interactable components.

FIG. 7 shows an example computing device 600 (e.g., a computer) that may be arranged in some embodiments to perform the methods (or portions thereof) described herein, such as by being configured as a controller of the perfusion modulating system. In a very basic configuration 602, computing device 600 generally includes one or more processors 604 and a system memory 606. A memory bus 608 may be used for communicating between processor 604 and system memory 606.

Depending on the desired configuration, processor 604 may be of any type including, but not limited to: a microprocessor ($\mu$P), a microcontroller ($\mu$C), a digital signal processor (DSP), or any combination thereof. Processor 604 may include one or more levels of caching, such as a level one cache 610 and a level two cache 612, a processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations, memory controller 618 may be an internal part of processor 604.

Depending on the desired configuration, system memory 606 may be of any type including, but not limited to: volatile memory (such as RAM), non-volatile memory (such as ROM, flash memory, etc.), or any combination thereof. System memory 606 may include an operating system 620, one or more applications 622, and program data 624. Application 622 may include a determination application 626 that is arranged to perform the operations as described herein, including those described with respect to methods described herein. The determination application 626 can obtain data, such as pressure, flow rate, and/or temperature, and then determine a change to the system to change the pressure, flow rate, and/or temperature.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include: magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include: volatile and non-volatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to: RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 646 includes a network controller 660, which may be arranged to facilitate communications with one or more other computing devices 662 over a network communication link via one or more communication ports 664.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 600 may also be implemented as a personal computer including both laptop computer and non-laptop computer configurations. The computing device 600 can also be any type of network computing device. The computing device 600 can also be an automated system as described herein.

The embodiments described herein may include the use of a special purpose or general-purpose computer including various computer hardware or software modules.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

In some embodiments, a computer program product can include a non-transient, tangible memory device having computer-executable instructions that when executed by a processor, cause performance of a method that can include: providing a dataset having object data for an object and condition data for a condition; processing the object data of the dataset to obtain latent object data and latent object-condition data with an object encoder; processing the condition data of the dataset to obtain latent condition data and latent condition-object data with a condition encoder; processing the latent object data and the latent object-condition data to obtain generated object data with an object decoder; processing the latent condition data and latent condition-object data to obtain generated condition data with a condition decoder; comparing the latent object-condition data to the latent-condition data to determine a difference; processing the latent object data and latent condition data and one of the latent object-condition data or latent condition-object data with a discriminator to obtain a discriminator value; selecting a selected object from the generated object data based on the generated object data, generated condition data, and the difference between the latent object-condition data and latent condition-object data; and providing the selected object in a report with a recommendation for validation of a physical form of the object. The non-transient, tangible memory device may also have other executable instructions for any of the methods or method steps described herein. Also, the instructions may be instructions to perform a non-computing task, such as synthesis of a molecule and or an experimental protocol for validating the molecule. Other executable instructions may also be provided.

EXPERIMENTAL

A component useful for mimicking the microenvironment of myocytes is to recreate the 3D matrix conditions found in vivo. In this context the device can use Matrigel in the myocyte chamber to create a 3D Matrix. Cardiac myocytes (e.g. from Lonza, Walkersville, Md.) can be cultured in cell culture medium. A Matrigel (Kleinman & Martin, 2005) solution can be introduced into the chamber from the inlet port of the chamber using a syringe pump and allowed to polymerize for 2 hours. Myocytes at a concentration of $5 \times 10^5$ cells/ml mixed with matrigel can be injected into the chamber and incubated at 37° C. and 5% CO2. Flow in the capillaries can be continuous at a shear rate of 15 $sec^{-1}$ to 500 $s^{-1}$. Media can be replaced using the programmable syringe pump (Harvard PHD 2000). Cell viability can be assayed using LIVE/DEAD® viability kits (Invitrogen, CA) with green stain indicating healthy cells and red unhealthy and decaying cells.

A wide variety of cells (e.g., endothelial, epithelial, ovarian, breast) can be cultured in the device. However, each cell type may need fine tuning of culture protocols for culture in these devices. Seeding density of the cells in addition concentration of matrigel can be varied to grow a uniform layer. Finally, media replacement time can be optimized to overcome any rapid buildup of waste products from the cells.

Measurement of Synchronized Beating and Contraction of Myocytes:

Beating exhibited by cardiac myocytes can be recorded using microscope connected to a camera. The procedure can be automated using software (e.g. NIKON Elements) to see if the beating of the myocytes is synchronized. The beats per minute can serve as the baseline for subsequent ischemia assays.

In order to access whether myocytes have intact contractile properties, electrodes can be inserted in the ports of the chamber and an electrical signal can be applied. Contraction length and duration can be recorded for the cells to serve as baseline following ischemia. A plot of % of cells exhibiting synchronized beating can be used to analyze experimental observations. The frequency, voltage and pulse duration being used to test the contraction properties can be varied to yield a plot of contraction length for cells.

Myocytes exchange oxygen and nutrients with the blood across the myocyte-capillary boundary. During normal behavior of blood flow, replacement of fresh nutrients keeps the waste products level low, but after an ischemia, it results in a shock to the myocytes. However, a common feature is that in the periphery of the ischemic zone, myocytes still have access to nutrients via capillaries whereas the area away from the capillaries becomes necrotic. The diffusion of the nutrients from the capillary to the center of the ischemic area is dependent on the consumption rate of the myocytes and the diffusion rate. In order to assess this diffusion the device can perform the following simulation and experiments.

Ischemic conditions can be subsequently generated in the device followed by experimental analysis on pH/hypoxia changes. The device can be used to assay ischemic myocytes using hypoxia markers; pimonidazole and HIF-1alpha; mitochondria depolarization using Mitotracker probe; inflammation using ICAM-1 and P-selectin; and finally for apoptotic regions using Tunnel and Caspase assays. The device can allow monitoring of the gradients for hypoxia regions using SNARF assays. In all experiments, the nucleus can be counterstained with Hoechst to monitor integrity of the cells. LIVE/DEAD® assay can be utilized as needed.

A general-purpose Computational Fluid Dynamics (CFD) code (e.g., CFD-ACE+), based on the Finite Volume Method (FVM) can be used to discretize and solve the governing equations for fluid flow and diffusion in the device. A three-dimensional computational mesh similar to the one shown in FIG. 5 can be generated by importing the AUTO-CAD layouts into CFD-GEOM, the grid generation module. The computation-ready geometry and meshes are then loaded into CFD-ACE+ for simulation. Modules of fluid flow and chemistry can be used. Flow rates mimicking the shear rates observed in capillaries during healthy and ischemic conditions can be simulated. The time taken for the cell culture medium to diffuse through the entire central chamber can be analyzed. Plot of diffusion time versus flow rate can be generated which can provide guidance during the experimental analysis following ischemia, hypoxia, and MI.

Experimental Diffusion in the Myocyte Chamber:

The myocyte chamber and the capillary channels can be primed with phosphate buffer. Fluorescent dye, FITC at a concentration of 1 µM can be injected into the capillary sections of the network. The diffusion rate of FITC from the capillary channels into the myocyte chamber can be recorded by taking time-lapse images of the device every 5 minutes till the chambers are completely filled. A second experiment can be run mimicking the ischemic condition. If the results between the experiments and simulation match well, one can use subsequent simulation runs as guidance for testing any new flow rates.

Modeling MI in the Developed Device:

A MI model can be provided in the device by ischemic shock for the myocytes. This assay can represent the scenario where blood flow (e.g., nutrients and oxygen) is hindered to the myocardium. Reperfusion can be started and the damage to the cardiac myocytes will be assessed. Changes in pH, upregulation of inflammation markers and viability can be measured.

Myocytes exchange oxygen and nutrients with the blood across the myocyte-capillary boundary. In the device, myocytes are initially fed by media replacement through the myocyte-capillary interface and the myocyte chamber itself. During normal behavior of blood flow, replacement of fresh nutrients keeps the waste products level low, but after ischemia, when the supply is limited due to reduced blood flow, it results in ischemic shock in the myocytes. However, a common feature observed in MI hearts is that in the periphery of the infarct, the myocytes still have access to nutrients via capillaries whereas the area away from the capillaries becomes necrotic. The diffusion of the nutrients from the capillary to the center of the infarct area is dependent on the rate of consumption by the myocytes and the diffusion rate. In order to assess this diffusion one can perform the simulations and experiments described herein.

Initiation of Ischemia and Reperfusion Injury in the Device:

Myocytes can be allowed to grow to confluence in the myocyte chamber to 80-90% confluency and synchronized beating. A this stage, media perfusion to the myocyte chamber can be stopped completely for 5 minutes, 30 minutes, 4 hours and 24 hours, respectively, to model ischemia and hypoxia. Two different conditions can be utilized. In the first, flow in the capillary channels can be continued (e.g., mimicking low ischemic conditions) during the period of media stoppage to the myocyte chamber. In the second set, flow in the capillary channels can also be stopped (e.g., severe ischemic conditions) for the duration of the blockage and switched back on at the respective time points. At respective end time points, cell conditions can be assayed for synchronized beating, intact contraction and viability. Control experiments with flow being normal in both the myocyte chamber and capillary channels can be performed. A plot of distance versus cells with synchronized beating from the capillary channel to the center of the chamber can be generated and compared to controls. Similarly, the reduction in the contractile length and the number of cells can be compared. Morphological analysis of the cells can be conducted using phase contrast microscopy.

Three distinct regions of ischemia can be induced as shown in FIG. 1A; (a) the ischemic zone 150 where the cells don't have access to fresh media and waste metabolites are present in excess specifically for the cells present in the center of the chamber, (b) the border zone 152 where partial cells experience excess waste metabolites and hypoxia whereas the other half of cells are viable, and finally (c) non-ischemic zone 154, where the cells have abundant supply of fresh nutrients near to the capillary channels.

An example of a method of creating hypoxia and reperfusion injury is shown in Table 1.

TABLE 1

Example to create hypoxia and then reperfusion injury.

| Tissue Chamber | Flow in Capillary | Time Point | Condition of Mimicked |
| --- | --- | --- | --- |
| Flow On | On (15 sec-1) | 5, 30 minute, 4 and 24 hr | Healthy Cells(Control) |
| Flow Off | On (15 sec-1) | 5, 30 minute, 4 and 24 hr | Low Level Ischemia |
| Flow Off | On (2.5 sec-1) | 5, 30 minute, 4 and 24 hr | Low to moderate Ischemia |
| Flow Off | Off and On (15 sec-1) | 5, 30 minute, 4 and 24 hr | Moderate Ischemia |
| Flow Off | Off and On (2.5 sec-1) | 5, 30 minute, 4 and 24 hr | Severe Ischemia |
| Flow On | On (15 sec-1) | 5, 30 minute, 4 and 24 hr | Reperfusion Injury |

The flow in capillary Off and On implies that the flow in capillary channel was also stopped during the stoppage of flow in the central chamber for the respective time points of 5 minutes, 30 minutes, 4 hours and 24 hours. However, at the end of these time points, flow in capillary channel was turned on and the cells were assayed for viability at 24 hour post flow being turned on. This mimics the reperfusion scenario observed in vivo.

One can look at alternative time points for the varying ischemic effects on the myocytes.

In any experiment described herein, the flow in the capillary channels and/or internal chamber can be restarted for reperfusion. The flow can be set to cause a reperfusion injury. Subsequent to the reperfusion injury, the cell culture can be analyzed for changes in pH, upregulation of inflammation markers and viability, and the parameters thereof can be measured. The parameters post reperfusion injury can then be compared to a control without reperfusion injury. Thus, information about the created reperfusion injury can be obtained.

Measurement of pH/Hypoxia Changes in the Myocyte Chamber:

Following ischemia and/or reperfusion injury, a gradient of hypoxia can be developed as the nutrients are not being replenished fast enough to the myocytes. This results in pH changes in regions of the myocardium or the myocyte chamber in the device. In order to access the varying pH/hypoxia conditions in the myocyte chamber, one can use the fluorescent pH indicator dye SNARF®-4F (Invitrogen, CA) which exhibits a significant pH-dependent emission shift (from yellow-orange to deep red fluorescence) and allows determination of hypoxic regions. The myocyte chamber can be injected with SNARF-4F at a concentration of 10 µM diluted in cell culture media. The entire chamber can be then divided into sections using virtual grids. Image analysis can be performed to yield areas with varying levels of pH changes by plotting distance from capillary channel versus intensity. The varying pH/hypoxia conditions in the myocyte chamber can be determined.

Pimonidazole Based Measurements:

Hypoxic cells in the co-culture can be detected using the Hypoxyprobe-1 Plus Kit (NPI Inc) according to the manufacturer's instructions. In brief, cells can be incubated with pimonidazole (400 µM) for 2 hr followed by fixation using 4% formaldehyde and permeabilized using 0.1% Triton X-100. After blocking with BSA, cells can be labeled with Hypoxyprobe Mab1-FITC (1:200). Nuclei will be stained with Hoechst followed by fluorescence imaging.

pH Indicator Dye Based Measurements:

SNARF®-4F (Invitrogen, CA) which exhibits a significant pH-dependent emission shift (from yellow-orange to deep red fluorescence) allows determination of hypoxic regions. The myocyte chamber can be injected with SNARF-4F (10 µM) and the resultant fluorescent intensity can be imaged.

The concentration of SNARF®-4F used (10 µM) is typical for monitoring pH gradients. However, in case the intensity levels are indistinguishable between the varying regions of the myocyte chamber, concentrations can be dropped or increased to get better signal to noise ratio of the pH gradients. Other SNARF dyes such as SNARF-1 and SNARF-5 can be utilized as needed.

Data can be measured by generation of a plot showing distinct gradients of hypoxia (pH changes) from the capillary channel to the center of the myocyte chamber. A three zone differential pattern of ischemia is expected with significant variations in the patterns following a low ischemia induced MI to a critical ischemia induced MI.

Biomarker Analysis in the Myocyte Chamber:

It is known that certain adhesion molecules such as ICAM-1 and P selectin are upregulated following MI on the myocytes. In addition, hypoxia-inducible factor-1 (HIF-1) is known to be upregulated in myocytes following hypoxic conditions. At regular time points of the ischemia experiments (Table 1), cells can be incubated with fluorescently tagged antibodies to ICAM-1 and HIF-1. The entire chamber can be divided into virtual grids to yield areas with differential expression of these markers. The location of these markers on the cells can be compared with the hypoxic regions from the SNARF assay to validate the zones of ischemia and the levels of biomarkers.

One can use antibodies to adhesion molecules (e.g. ICAM-1) to assess the % of cells expressing the inflammation marker and their location in the entire chamber. 2 µm fluorescent microspheres (Polysciences Inc., Warrington, Pa.) at a concentration of $2\times10^8$ particles/ml can be coated with anti-ICAM-1 (BD Biosciences, San Jose, Calif.). Microspheres washed 2× in 0.1 M NaHCO3 buffer pH 9.2 can be incubated with Protein A (Zymed, Carlsbad, Calif.) at a concentration of 300 µg/ml and incubated at room temperature overnight to saturate the surface of the microsphere. The following day, a 2× wash with solution containing 1% BSA in HBSS can be performed. The microspheres can be resuspended in 1% BSA in HBSS and incubated at room temperature for 20 minutes. Following incubation and subsequent 2× wash with buffer, anti-ICAM-1 antibody at a concentration of 100 µg/ml diluted in 1% BSA/HBSS can be mixed with the microspheres. Protein A binds the Fc fragment of the antibody to allow proper orientation of the antibody. The microspheres can be held in this solution at 4° C. until experimentation. Prior to experiments, microspheres can be washed twice with 1% BSA and HBSS. A control set of microspheres with IgG coating can also be prepared. The prepared particles can be injected into the myocyte chamber diluted in cell culture media to a concentration of $10^6$ particles/ml at the time point showing maximum MI. Following incubation period (e.g., 30 minutes), a wash can be performed with PBS and the cells will be imaged.

Apoptotic Assays:

Cells under hypoxia are subject to stress eventually leading to apoptosis. Hence, they can be monitored using Tunnel (measurement of nuclear DNA fragmentation), or Caspase (caspase activity in apoptotic cells) assay. Cells can be fixed with 4% paraformaldehyde for 1 hr and permeabilized in 0.1% Triton-100, 0.1% sodium citrate (4° C. for 2 min) followed by incubation with TUNEL reaction mixture (1 hr at 37° C.). After washing, cells can be incubated with alkaline phosphatase-conjugated antibody (30 min at 37° C.) followed by counterstained with hematoxylin. For Caspase assay, the cells can be incubated with the reaction solution (1 hr at 37° C.) followed by a wash and counterstaining with Hoechst dye. We can also use Mitotracker red (stains mitochondria) for determining depolarization of cells following hypoxia.

As before, the chamber can be divided into virtual grids to yield areas with differential expression of the markers. The locations of the fluorescence images can be correlated with the SNARF and pimonidazole images to validate the hypoxia regions and zones of ischemia.

In addition, one can perform gene expression analysis (RT-PCR) to validate the upregulation of the hypoxia and inflammation markers. Finally, one can explore whole genome arrays to identify upregulated genes for the different regimes of ischemia.

Transport Model for Prediction of Hypoxia and Regeneration Following MI:

A morphologically realistic mathematical model of oxygen transport in cardiac tissue following infarction can be used to supplement the experimental studies. The model utilizes microvascular morphology of cardiac tissue based on available morphometric images to simulate experimentally measured oxygen levels after MI. Model simulations of relative oxygenation match experimental measurements closely and can be used to simulate distributions of oxygen concentration in normal and infarcted hearts of rodents. 3,3-diheptyloxacarbocyanine iodide (DiOC7) and CD31 staining can be used to measure the number of anatomic and perfused vessels. Hypoxia levels can be measured by the use of EFS (a pentafluorinated derivative of etanidazole) that is preferentially metabolized in hypoxia cells.

Viability of Myocytes:

In order to assess the viability and healthy condition of the myocytes in the microfluidic device, one can use a combination of fluorescent dyes. Propidium iodide (Invitrogen, CA), an indicator of membrane leakiness and cell death in combination with SYTO16 (viable cell indicator) are commonly used to assess cell viability. Propidium iodide and SYTO16 at a concentration of 0.5 µg/mL in cell culture medium can be injected into the myocyte chamber. After 15 minutes of incubation, images of the cells can be acquired using epi-fluorescence microscopy. The % of cells showing uptake of propidium iodide (stain in red) can indicate cells not in healthy condition, whereas cells staining with SYTO16 (stain green) indicate healthy cells. This method can be used to ascertain % of viable cells following MI and/or reperfusion injury in the device.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In one embodiment, the present methods can include aspects performed on a computing system. As such, the computing system can include a memory device that has the computer-executable instructions for performing the method. The computer-executable instructions can be part of a computer program product that includes one or more algorithms for performing any of the methods of any of the claims.

In one embodiment, any of the operations, processes, methods, or steps described herein can be implemented as computer-readable instructions stored on a computer-readable medium. The computer-readable instructions can be executed by a processor of a wide range of computing systems.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

This patent document incorporates by specific reference in their entirety the following patents and patent applications: U.S. Pat. Nos. 7,725,267; 8,355,876; 8,175,814; 8,380,443; 8,417,465; 8,589,083; U.S. 2010/0227312; PCT/US2013/072081; U.S. 2013/0101991; and U.S. 2013/0149735. These applications provide background and state of the art as well as definitions for terms of art.

The invention claimed is:

1. A method of creating a reperfusion injury, the method comprising:
    providing a cell culture device having an internal chamber with at least one port coupled to a perfusion modulating system capable of modulating perfusion in the internal chamber, wherein the internal chamber includes a cell culture;
    perfusing a fluid through the internal chamber with the perfusion modulating system, wherein the perfusion modulating system includes at least one pump;
    reducing fluid flow through the internal chamber;
    reperfusing the fluid flow through the internal chamber; and
    creating the reperfusion injury in the cell culture by reperfusing the fluid flow through the internal chamber.

2. The method of claim 1, wherein the cell culture includes at least one type of tissue cells.

3. The method of claim 2, wherein the at least one type of tissue cells includes myocytes, neurons, nephrons, hepatocytes and intestinal epithelial cells.

4. The method of claim 1, wherein the fluid includes a liquid carrier having oxygen.

5. The method of claim 1, further comprising varying intensity of the perfusion or duration of the perfusion by changing flow rate of the fluid.

6. The method of claim 1, further comprising creating hypoxia in the cell culture from the reduced reducing the fluid flow.

7. The method of claim 1, further comprising occluding the fluid flow prior to the reperfusing.

8. The method of claim 1, further comprising determining an effect of reperfusing on the cell culture based on the reperfusion injury.

9. The method of claim 1, further comprising:
at least one fluid channel bordering the internal chamber of the cell culture device; and
at least one wall separating the internal chamber and the at least one fluid channel, wherein the at least one wall includes at least one gap, each gap fluidly coupling the internal chamber with the at least one fluid channel.

10. The method of claim 1, wherein the perfusion modulating system is fluidly coupled to the at least one port in the cell culture device.

11. The method of claim 10, wherein the at least one port in the cell culture device is in at least one fluid channel that borders the internal chamber.

12. The method of claim 10, wherein the at least one port in the cell culture device is in the internal chamber.

13. The method of claim 1, further comprising monitoring the cell culture during the steps of perfusing the fluid flow through the internal chamber, reducing the fluid flow through the internal chamber, and reperfusing the fluid flow through the internal chamber.

14. The method of claim 13, further comprising monitoring the cell culture with electrodes in the internal chamber.

15. The method of claim 13, further comprising performing impedance measurements on the cell culture.

16. The method of claim 1, further comprising assessing damage of the cell culture from reperfusing by determining: changes in pH, upregulation of inflammation markers, increase in reactive oxygen species, changes in intracellular calcium, microvascular dysfunction, epithelial cell disfunction, altered cellular metabolism, activation of neutrophils, activation of platelets, activation of complement factors and proteases, increase in eicosanoids, increase in nitric oxide, increase in endothelin, increase in cytokines, or viability of cells of the cell culture.

17. The method of claim 1, further comprising:
introducing a test substance to the internal chamber before, during or after the reperfusion injury; and
screening the cell culture for changes in response to the test substance.

18. The method of claim 14, wherein the electrodes are 3D electrodes.

19. The method of claim 1, wherein the cell culture includes a tissue construct of porous 3D matrix comprised of hydrogel and/or extracellular matrix, wherein the hydrogel and/or extracellular matrix is derived from a natural component or synthetic component.

20. The method of claim 19, wherein the tissue construct includes:
one or more three-dimensional electrodes inserted into the tissue construct; and/or
one or more fluid flow channels passing through the tissue construct, the one or more fluid flow channels including one or more apertures to allow for perfusion of the fluid into the tissue construct.

21. The method of claim 17, further comprising determining a mechanism of action of the test substance on the cell culture based on the changes in response to the test substance.

* * * * *